United States Patent [19]
Smith et al.

[11] Patent Number: 6,100,975
[45] Date of Patent: *Aug. 8, 2000

[54] RAMAN SPECTROSCOPY APPARATUS AND METHOD USING EXTERNAL CAVITY LASER FOR CONTINUOUS CHEMICAL ANALYSIS OF SAMPLE STREAMS

[75] Inventors: Lee M. Smith, Salt Lake City; Robert E. Benner, Holladay, both of Utah; George R. Gray, Apple Valley, Minn.; Ming-Wei Pan, Salt Lake City; Richard D. Rallison, Paradise, both of Utah

[73] Assignees: Process Instruments, Inc.; The University of Utah Research Foundation, both of Salt Lake City, Utah

[ * ] Notice: This patent issued on a continued prosecution application filed under 37 CFR 1.53(d), and is subject to the twenty year patent term provisions of 35 U.S.C. 154(a)(2).

[21] Appl. No.: 09/054,588

[22] Filed: Apr. 3, 1998

Related U.S. Application Data

[63] Continuation-in-part of application No. 08/647,586, May 13, 1996, Pat. No. 5,751,415.

[51] Int. Cl.[7] .......................................................... G01J 3/44
[52] U.S. Cl. .............................. 356/301; 356/328; 372/92
[58] Field of Search ...................... 356/301, 70, 317–318, 356/300, 328, 334, 440, 417, 436, 73; 250/227.23, 573, 574; 372/92, 20, 22, 23, 102, 98–99, 108, 32

[56] References Cited

U.S. PATENT DOCUMENTS 3,906,241   9/1975   Thompson .
4,416,505   11/1983  Dickson .
4,530,564   7/1985   Close .

(List continued on next page.)

FOREIGN PATENT DOCUMENTS 228 990     10/1985   Germany .
56-55842    5/1981    Japan .
1-287448    11/1989   Japan .

OTHER PUBLICATIONS

"SDL–8530—785 nm, 300 mW cw Wavelength–Stabilized High Power Laser Diode System," *SDL Product Catalog*, pp. C5–C7 (1996/1997).

Mark D. Weiss, "NMR and Raman Spectroscopies Move from Lab to Plant," *Today's Chemist at Work*, pp. 25–28, (Jan. 1995).

W. R. Kalsi, A. S. Sarpal, S. K. Jain, S. P. Srivastava, and A. K. Bhatnagar, "Determination of Oxygenates in Gasoline by 1H Nuclear Magnetic Resonance Spectroscopy," *Energy & Fuels*, pp. 574–579 (May 4, 1995).

(List continued on next page.)

*Primary Examiner*—K. P. Hantis
*Attorney, Agent, or Firm*—Madson & Metcalf

[57] ABSTRACT

Raman spectrometer for analyzing the chemical composition of sample streams using an external cavity laser light source is disclosed. The laser provides an effective light source useful in continuously analyzing a sample stream containing petroleum products, aqueous or biological fluids, or solid slurries. The light is introduced into a bundle of optical fibers connected to a Raman sample cell. The Raman sample cell is configured to allow continuous sample flow therethrough. Scattered light from the sample cell preferably exits the optical fibers as a linear optical signal. A Raman spectrometer passes the optical signal through an excitation wavelength filter, an optical slit, and a volume holographic transmission grating with an aberration correction device before transmitting the optical signal to a charge coupled device array which converts the optical signal into a electronic signal. The electronic signal is analyzed and converted by computer into a representation of the chemical analysis of the sample stream.

53 Claims, 23 Drawing Sheets

U.S. PATENT DOCUMENTS

| | | |
|---|---|---|
| 4,540,280 | 9/1985 | Anderson et al. . |
| 4,573,761 | 3/1986 | McLachlan et al. . |
| 4,579,457 | 4/1986 | Guigues . |
| 4,630,923 | 12/1986 | Tans et al. . |
| 4,688,879 | 8/1987 | Fairchild . |
| 4,783,168 | 11/1988 | Florisson et al. . |
| 4,786,171 | 11/1988 | LeFebre et al. . |
| 4,818,045 | 4/1989 | Chang . |
| 4,830,441 | 5/1989 | Chang . |
| 4,867,559 | 9/1989 | Bach . |
| 4,879,167 | 11/1989 | Chang . |
| 4,884,276 | 11/1989 | Dixon et al. . |
| 4,895,445 | 1/1990 | Granger . |
| 4,896,325 | 1/1990 | Coldren . |
| 4,917,491 | 4/1990 | Ring et al. . |
| 4,937,448 | 6/1990 | Mantz et al. . |
| 4,943,971 | 7/1990 | Fiet et al. . |
| 4,963,745 | 10/1990 | Maggard . |
| 4,973,561 | 11/1990 | Hansen et al. . |
| 4,978,182 | 12/1990 | Tedesco . |
| 4,990,780 | 2/1991 | Lee et al. . |
| 4,995,050 | 2/1991 | Waarts et al. . |
| 5,011,284 | 4/1991 | Tedesco et al. . |
| 5,015,049 | 5/1991 | Chang . |
| 5,022,038 | 6/1991 | Bradley . |
| 5,028,563 | 7/1991 | Feit et al. . |
| 5,058,124 | 10/1991 | Cameron et al. . |
| 5,071,208 | 12/1991 | Chang . |
| 5,077,481 | 12/1991 | Hoult . |
| 5,103,453 | 4/1992 | Kebabian et al. . |
| 5,112,127 | 5/1992 | Carrabba et al. . |
| 5,119,338 | 6/1992 | Saito . |
| 5,124,815 | 6/1992 | Chang . |
| 5,139,334 | 8/1992 | Clarke . |
| 5,166,747 | 11/1992 | Schroeder et al. . |
| 5,170,056 | 12/1992 | Berard et al. . |
| 5,179,630 | 1/1993 | Chang et al. . |
| 5,194,910 | 3/1993 | Kirkpatrick, Jr. et al. . |
| 5,220,401 | 6/1993 | Milsevic et al. . |
| 5,225,679 | 7/1993 | Clarke et al. . |
| 5,319,668 | 6/1994 | Luecke . |
| 5,348,645 | 9/1994 | Maggard et al. . |
| 5,349,188 | 9/1994 | Maggard . |
| 5,349,189 | 9/1994 | Maggard . |
| 5,360,972 | 11/1994 | DiFoggio et al. . |
| 5,362,965 | 11/1994 | Maggard . |
| 5,377,004 | 12/1994 | Owen et al. . |
| 5,379,310 | 1/1995 | Papen et al. . |
| 5,381,237 | 1/1995 | Sela . |
| 5,386,426 | 1/1995 | Stephens . |
| 5,402,241 | 3/1995 | Jeannotte et al. . |
| 5,404,218 | 4/1995 | Nave et al. . |
| 5,418,631 | 5/1995 | Tedesco . |
| 5,424,825 | 6/1995 | Delhaye et al. . |
| 5,434,874 | 7/1995 | Fouquet et al. . |
| 5,442,439 | 8/1995 | Battey et al. . |
| 5,455,673 | 10/1995 | Alsmeyer et al. . |
| 5,471,327 | 11/1995 | Tedesco et al. . |
| 5,524,012 | 6/1996 | Wang et al. . |
| 5,530,565 | 6/1996 | Owen . |
| 5,559,597 | 9/1996 | Battey et al. . |
| 5,587,847 | 12/1996 | Chang et al. . |
| 5,596,196 | 1/1997 | Cooper et al. . |
| 5,610,836 | 3/1997 | Alsmeyer et al. . |
| 5,638,172 | 6/1997 | Alsmeyer et al. . |
| 5,642,375 | 6/1997 | King et al. . |
| 5,644,396 | 7/1997 | Hopkins, II . |
| 5,652,653 | 7/1997 | Alsmeyer et al. . |
| 5,657,120 | 8/1997 | Smith . |
| 5,657,404 | 8/1997 | Buchanan et al. . |
| 5,691,989 | 11/1997 | Rakuljic et al. . |
| 5,731,873 | 3/1998 | Brown et al. . |
| 5,751,415 | 5/1998 | Smith et al. . |
| 5,771,252 | 6/1998 | Lang et al. . |
| 5,802,085 | 9/1998 | Lefevre et al. . |
| 5,850,623 | 12/1998 | Carman, Jr. et al. . |

OTHER PUBLICATIONS

Gilmore et al., "Quantitative Detection of Environmentally Important Dyes . . . Spectroscopy," *Applied Spectroscopy*, vol. 49, No. 4, pp. 508–512 (1995).

Andrew J. Vreugdenhil and Ian S. Butler, "Detection of the Engine Anti–knock Additive Methylcyclopentadienyl Manganese Tricarbonyl (MMT) from Unleaded Gasoline in Soil by Diffuse Reflectance Infrared Fourier Transfer Spectroscopy and Mass Spectroscopy," *Applied Spectroscopy*, vol. 49 No. 4, pp. 482–485 (1995).

Christopher J. de Bakker and Peter M. Fredericks, "Determination of Petroleum Properties by Fiber–Optic Fourier Transform Raman Spectrometry and Partial Least–Squares Analysis, " *Applied Spectroscopy*, vol. 49, No. 4, pp. 1766–1771 (1995).

John B. Cooper, Philip E. Flecher, Thomas M. Vess, and William T. Welch, "Remote Fiber–Optic Raman Analysis of Xylene Isomers in Mock Petroleum Fuels Using a Low–Cost Dispersive Instrument and Partial Least–Squares Regression Analysis." *Applied Spectroscopy*, vol. 49, No. 5 (1995).

John B. Cooper, Kent L. Wise, James Groves, and William T. Welch, "Determination of Octane Numbers and Reid Vapor Pressure of Commercial Petroleum Fuels Using FT–Raman Spectroscopy and Partial Least–Squares Regression Analysis," *Analytical Chemistry*, vol. 67, pp. 4095–4100 (1995).

Hillary L. MacDonald, Hao Liu, and Paul Yager, "Fiber Optic Sensor for General Anesthetics based on Raman Spectroscopy," *SPIE*, vol. 2131, pp. 514–524 (1994).

*Official Gazette* publication of Patent No. 5,363,463, p. 1302 (Nov. 8, 1994).

Francisco X. Garcia, Lola De Lima, and Julio C. Medina, "Determination of Methanol and Methyl tert–Butyl Ether in Gasoline by Infrared Spectroscopy Using The Circle® Cell and Multivariate Calibration," *Applied Spectroscopy*, pp. 1036–1039 (1993).

Maximo Gallignani, Salvador Garrigues, and Miguel de la Guardia, "Direct Determination of Benzene in Gasoline by Flow–Injection Fourier Transform Infrared Spectrometry," pp. 267–274 (Amsterdam 1993).

*Official Gazette* publicatiion of Patent No. 5,112,127, p. 912 (May 12, 1992).

Chen Zhaohui and Feng Xinlu, "Using NIR Spectroscopy for On–Line Gasoline Analysis," *Hydrocarbon Processing*, pp. 94–96 (Jan. 1992).

Cathy D. Newman, Georges G. Bret, and Richard L. McCrery, "Fiber–Optic Sampling Combined with an Imaging Spectrograph for Routine Raman Spectroscopy," *Applied Spectroscopy*, vol. 46, No. 2, pp. 262–265 (1992).

S. Michael Angel, Thomas M. Vess, and Michael L. Myrick, "Simultaneous Multi–point Fiber–optic Raman Sampling for Chemical Process Control Using Diode Lasers and a CCD Detector," *SPIE* (*Chemical, Biochemical, and Environmental Fiber Sensors III*), vol. 1587, pp. 219–231 (1991).

Kenneth P. J. Williams, Rupert E. Aries, David J. Cutler, and David P. Lidiard, "Determination of Gas Oil Cetane Number and Cetane Index Using Near–Infrared Fourier Transform Raman Spectroscopy," *Analytical Chemistry*, vol. 62, No. 23, pp. 2553–2556 (Dec. 1, 1990).

Yan Wang and Richard L. McCreery, "Evaluation of a Diode Laser/Charge Coupled Device Spectrometer for Near–Infrared RamanSpectroscopy," *Analytical Chemistry*, vol. 61 No. 23, pp. 2647–2651 (Dec. 1, 1989).

M. B. Seasholtz, D. D. Archibald, A. Lorber, and B. R. Kowalski, "Quantitative Analysis of Liquid Fuel Mixtures with the Use of Fourier Transform Near–IR Raman Spectroscoy," *Applied Spectroscopy*, vol. 43, No. 6, pp. 1067–1072 (1989).

*Official Gazette* publication of Patent No. 4,858, 238, p. 2092 (Aug. 15, 1989).

*Official Gazette* publication of Patent No. 4, 645,340 (Feb. 24, 1987).

Scott D. Schwab and Richard L. McCreery, "Remote, Long–Pathlength Cell for High–Sensitivity Raman Spectroscopy," *Applied Spectroscopy*, vol. 41, No. 1, pp. 126–130 (1987).

*Official Gazette* publication of Patent No. 4,630,923, p. 2022 (Dec. 23, 1986).

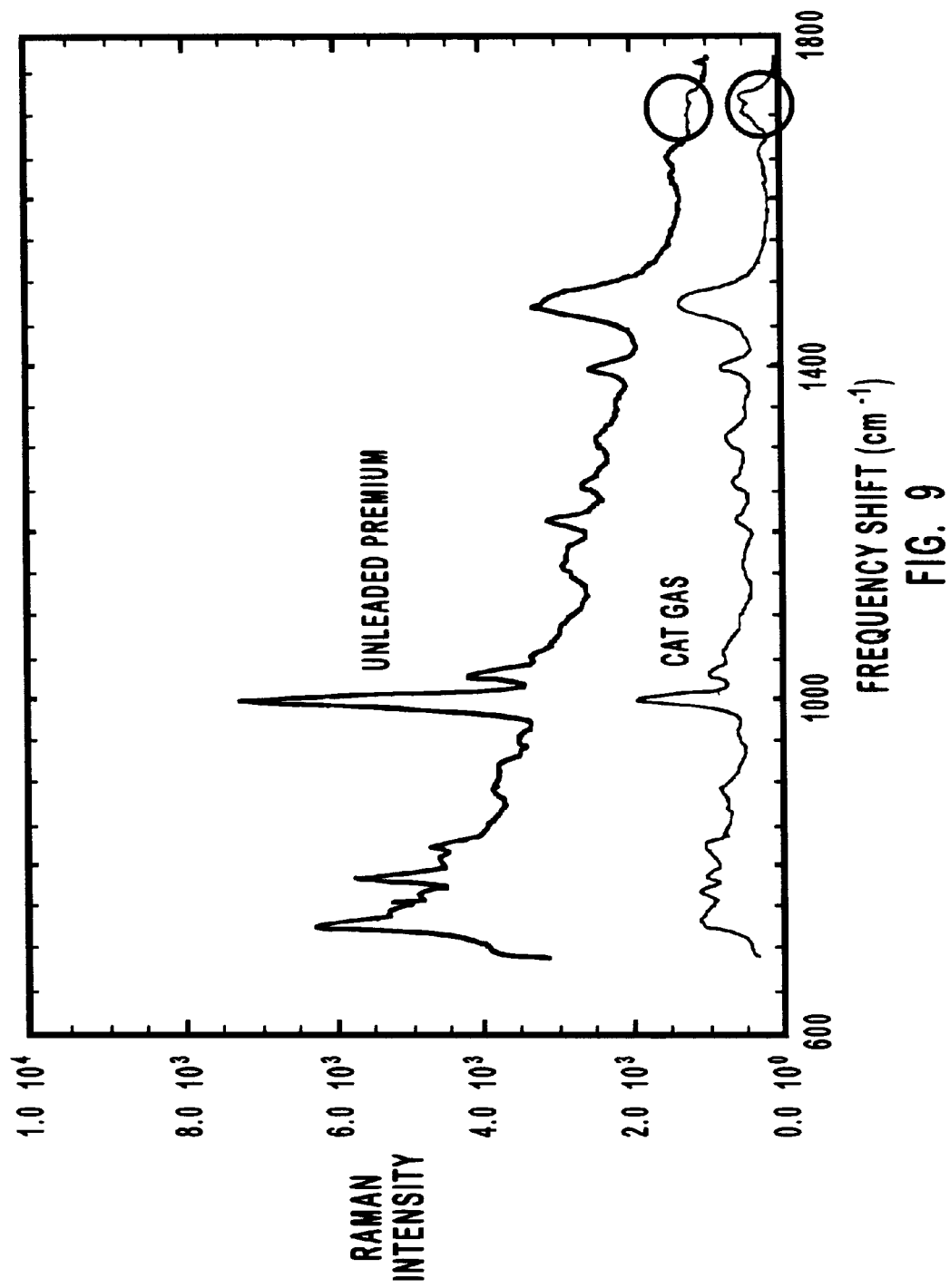

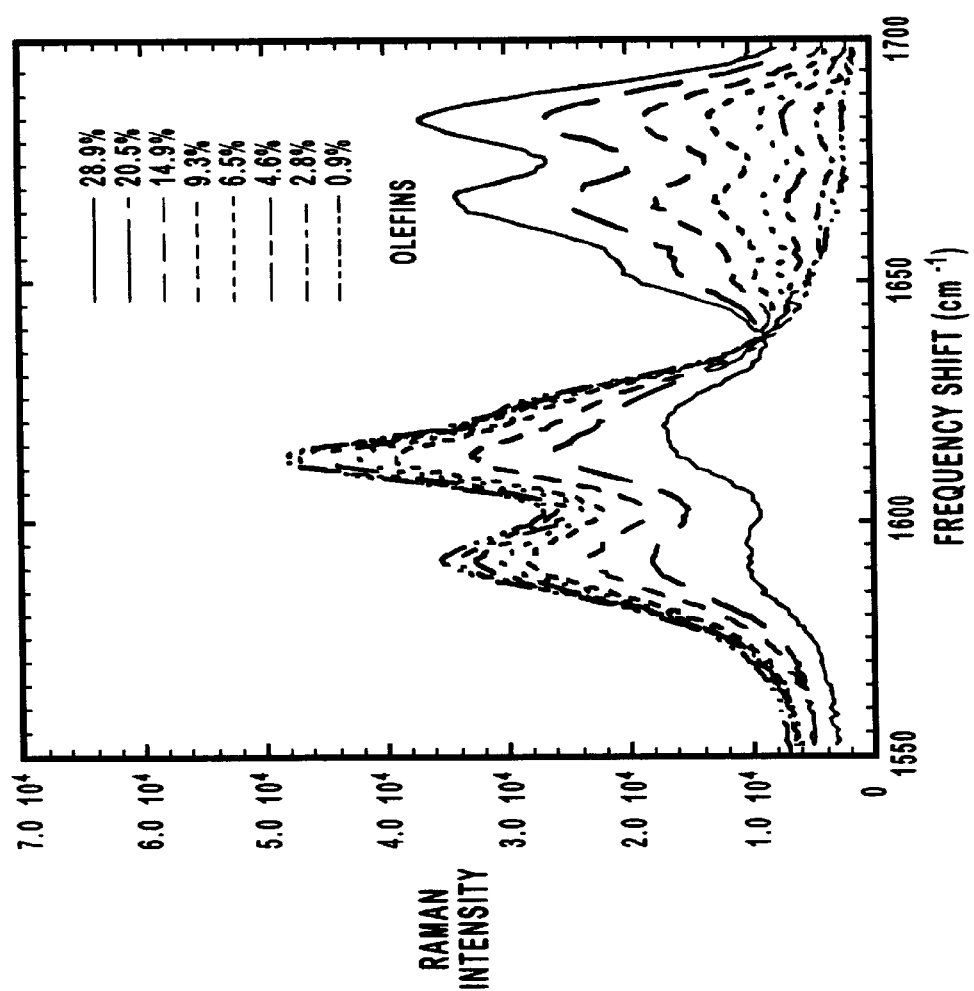

RAMAN SPECTROSCOPY APPARATUS AND METHOD USING EXTERNAL CAVITY LASER FOR CONTINUOUS CHEMICAL ANALYSIS OF SAMPLE STREAMS

RELATED APPLICATION

This invention is a continuation-in-part of U.S. patent application Ser. No. 08/647,586, filed May 13, 1996 U.S. Pat. No. 5,751,415, titled "Raman Spectroscopy Apparatus and Method for Continuous Chemical Analysis of Fluid Streams," which application is incorporated herein by reference.

GOVERNMENT RIGHTS

This invention was made with Government support under SBIR contracts No. F29601-96-C-0029 and No. F29601-96-C-0048 awarded by The Department of Defense, and National Science Foundation STTR Grant No. DMI-9522728.

FIELD OF THE INVENTION

The present invention is includes a novel apparatus and method for continuous chemical analysis of fluid streams, particularly fluid streams containing petroleum products, using Raman spectroscopy, using an external cavity laser as the light source. The Raman spectrometer can also be applied equally well to aqueous streams, biological samples, and solid slurries.

TECHNOLOGY BACKGROUND

The refining and processing of crude petroleum into commercially useful petroleum products is a vital industry around the world. One of the most important petroleum products is the class of gasoline fuels. Gasoline fuels consist of a mixture of various hydrocarbon compounds. The concentration and chemical grouping of these hydrocarbon compounds determines the resulting fuel properties such as octane number and Reid vapor pressure (RVP).

Reid vapor pressure provides a volatility measurement of the gasoline. The octane number for a gasoline fuel is defined in terms of its knocking characteristics relative to a standard blend of isooctane (2,3,4-trimethylpentane) and n-heptane. Arbitrarily, an octane number of zero has been assigned to n-heptane and a rating of 100 to isooctane. Thus, an unknown fuel having a knocking tendency equal to a blend of 90% isooctane and 10% n-heptane, by volume, is assigned an octane number of 90.

During the manufacture of various grades of gasoline, it is useful to monitor the final product to be sure it possesses the desired physical properties, such as octane number. However, there currently is not a quick and inexpensive system for continuously monitoring a gasoline fuel composition. Instead periodic samples are normally taken from the process stream and analyzed. Occasionally, a gasoline fuel blend sold at one octane rating actually has a higher octane rating. This is uneconomical, since higher octane gasolines are more valuable to the refinery than lower octane gasolines.

It is also useful to control the concentration of various hydrocarbon ingredients in the gasoline blend. For instance, it is desirable to reduce the concentration of benzene, a known carcinogen, in gasoline. Yet, benzene concentration is often difficult to measure using conventional analysis. It is also desirable to minimize the olefin concentration. Olefins are unsaturated hydrocarbons (containing C=C bonds) which are photoreactive and contribute to smog formation. Olefins are also hard to measure accurately using conventional techniques. Finally, because xylene is a valuable gasoline ingredient, excess xylene should be minimized. It also would be valuable to identify and quantify the xylene isomers (para, meta, and ortho) present in the gasoline, but conventional analytical techniques cannot quickly distinguish between the xylene isomers. Thus, it would be a significant advancement in the art to permit continuous monitoring of the gasoline's chemical composition and physical properties.

Concentrated sulfuric acid is used by refineries in the alkylation process. The sulfuric acid concentration needs to be carefully controlled between 90% and 98% during the alkylation process. Currently, refineries manually take individual "grab-samples." Because of the unreacted hydrocarbon contamination in the acid, the samples require centrifuging to separate the acid. The acid is then titrated in the laboratory to determine exact acid content. These tests are typically run every four hours. Because of the time constraints with this type of testing, the refineries tend to run much higher acid concentrations than they would like to ensure that the process proceeds uninterrupted. Maintaining an excessively high acid concentration costs millions of dollars annually at each refinery.

When the acid concentration reaches 89%, it is removed from the process and hauled back to a chemical plant for recycling. This process of constantly removing, adding and transporting concentrated sulfuric acid is expensive and potentially dangerous. Because of the high cost of sulfuric acid, Amoco Oil Company calculates that for each 0.5% drop in average acid content in their alkylation process, they could save $5,000,000 per year throughout their entire production system. It is estimated that a continuous, on-line, analysis of acid concentration would enable the average acid concentration to be reduced by about 1%. Taking into account the additional savings from reduced transportation and handling costs, this total savings could average $12,000,000 per year for Amoco Oil. The sulfuric acid concentration problem is universal for the petroleum industry, and it has been estimated that a continuous, on-line chemical stream analysis could save the U.S. petroleum industry over $100,000,000 annually, with some of this savings returning to customers.

The alkylation process does not react the same with all alkene compounds; propylene compounds for instance, react much differently than do most other alkenes. The alkylation process needs a rapid, on-line control to properly react to changing feed stocks, to efficiently adjust acid levels, and economically produce petroleum products from a wide variety of incoming crude oil. Thus, there is a significant need in the art for a process and method which allows on-line analysis and control of acid content of such process streams.

Raman spectroscopy is an analytical technique which uses light scattering to identify and quantify molecules. When light of a single wavelength (monochromatic) interacts with a molecule, the light scattered by the molecule contains small amounts of light with wavelengths different from the incident light. The wavelengths present in the scattered light are characteristic of the structure of the molecule, and the intensity of this light is dependent on the concentration of these molecules. Thus, the identities and concentrations of various molecules in a substance can be determined by illuminating the substance with monochromatic light and then measuring the individual wavelengths and their intensities in the scattered light.

A continuing problem with Raman spectroscopy is the very low intensity of the scattered light compared to the incident light. Elaborate spectrometers, having high light gathering power and dispersion, high stray light rejection, and sensitive detectors, are required to isolate and measure the low intensity Raman scattered light. These instruments are costly and delicate, and are not well suited for use in industrial manufacturing or processing facilities. As a result, they have rarely been used outside of laboratory environments. Improvements in the fields of lasers, optical fibers, and filters enable one to remotely locate a fiber-optic probe from its laser light source and from its spectrometer.

It will be appreciated that there is a need in the art for an apparatus and method for analyzing industrial fluid streams, particularly those containing petroleum products, which provides quick and accurate results.

SUMMARY OF THE INVENTION

The present invention is directed to an apparatus and method for analyzing the composition of a sample using Raman spectroscopy. Novel external cavity laser sources for use in Raman spectrometers are disclosed. The invention is particularly useful in continuously analyzing a fluid stream containing petroleum products, such as gasoline fuel or natural gas, biological liquids and solid slurries.

The apparatus includes a laser source for producing light having an excitation wavelength. Although conventional diode lasers can be used as the light source in the Raman spectrometer, it is presently preferred to use an external cavity diode laser. The light output from the external cavity diode laser can be controlled to provide a powerful, yet stable light output compared to typical single mode diode lasers. Although current Raman spectrometers use very narrow linewidth lasers, the broader linewidth obtained with the external cavity laser is adequate for the uses contemplated herein.

The light is preferably introduced into an excitation optical fiber which is combined with one or more collection optical fibers to form a bundle of optical fibers. The fiber bundle is optically connected to a Raman sample cell. The sample cell is preferably configured to allow continuous sample fluid flow therethrough.

Light from the excitation optical fiber is coupled into the sample cell, and backscattered Raman signal (light) from the sample cell is coupled into the one or more collection optical fibers. Alternatively, light from the laser source can be focussed directly into the sample cell. The optical fiber bundle is preferably separated from the flowing sample within the sample cell by an optional transparent fluid barrier (an optical window and or lens assembly).

In one presently Raman sample cell, the excitation light enters the cell through a transparent fluid barrier and interacts with the sample to be characterized. The light is absorbed by a color glass filter designed to absorb the excitation wavelength light. The filter is preferably oriented on a slight angle to minimize the amount of reflected laser light which enters the collection fibers. Raman scattered light emanating from the sample volume is guided down the one or more collection fibers to the Raman spectrometer. The Raman sample cell is not flow dependent, and it can be made with an practical internal volume, such as between 1 cc and 20 cc. The longer the sample cell, that is, the greater the distance between the input fiber and the absorbing filter, the more Raman interaction and consequently the greater the Raman signal.

In another embodiment within the scope of the present invention, the Raman sample cell is lined with a material having an index of refraction less than the index of refraction of the sample stream so that light reflects internally at the interface between the sample and the sample cell liner. This eliminates light losses which would otherwise occur if the light passed through the liner and was reflected at the exterior (air interface) surface of the liner.

Scattered light from the sample cell enters one or more collection optical fibers for transmission to a Raman spectrometer. Where a plurality of collection optical fibers are used, the fibers are preferably oriented parallel to the axis at which light passes through the Raman spectrometer. The exit ends of the collection fibers are preferably aligned in a linear array so that a linear optical signal is generated. The Raman spectrometer passes the optical signal through a filter to eliminate portions of the optical signal having the excitation wavelength. The optical signal is also passed through an optional optical slit. If a linear optical signal is generated, the optical slit preferably has dimensions comparable to the linear array of collection optical fibers. Orienting the exit ends of the optical fibers in a linear array can perform the same function as the optical slit by generating a linear optical signal. A commercially available charge coupled device converts the optical signal into a corresponding electronic signal to be analyzed by a computer and converted into a representation of the chemical analysis of the fluid stream.

A plurality of optical lenses are preferably provided to receive and convey the optical signal from the collection optical fibers, through the Raman spectrometer, to the charge coupled device. A volume holographic transmission grating is used to disperse the signal, and an aberration correction element is provided to correct optical aberrations introduced into the optical signal by the volume holographic grating element. A pair of 45 degree, right angle prisms is one presently preferred aberration correction element. Other optically transparent components such as wedges can be used for aberration correction. If necessary, the focusing function of the optical lenses can be performed with the holographic grating.

The use of an aberration correction element in combination with a volume holographic transmission grating can be used in conventional Raman spectrometers without a flowthrough sample cell or optical fibers. In such cases, solid or non-fluid samples are analyzed using conventional techniques, and the volume holographic transmission grating and aberration correction element provide the unique advantages described herein.

Through use of the optical fiber bundle, it is possible to locate the Raman sample cell in a remote location near an industrial process stream. The Raman spectrometer, laser source, and computer can be located in a distant, protected environment. The apparatus and method for analyzing the composition of a fluid stream using Raman spectroscopy is rapid and accurate. It has been shown to provide excellent analysis of fluid streams containing petroleum products. Of course, those skilled in the art will appreciate that the present invention can be readily adapted for use in analyzing other sample streams such as aqueous streams, biological samples, and solid slurries.

DESCRIPTION OF THE DRAWINGS

FIG. 9 is a graph of the Raman spectra of two different types of gasoline product, "cat gas" and unleaded premium (ULP), and the relative location of the olefin peaks at 1625 $cm^{-1}$ to 1725 $cm^{-1}$.

FIG. 10 is a graph of the Raman spectra of the gasolines analyzed in FIG. 9 with an expanded peak in the region from 1625 $cm^{-1}$ to 1725 $cm^{-1}$ as the olefin concentration is increased from 0.9% to almost 29%.

DETAILED DESCRIPTION OF THE PREFERRED EMBODIMENTS

Figure 1:
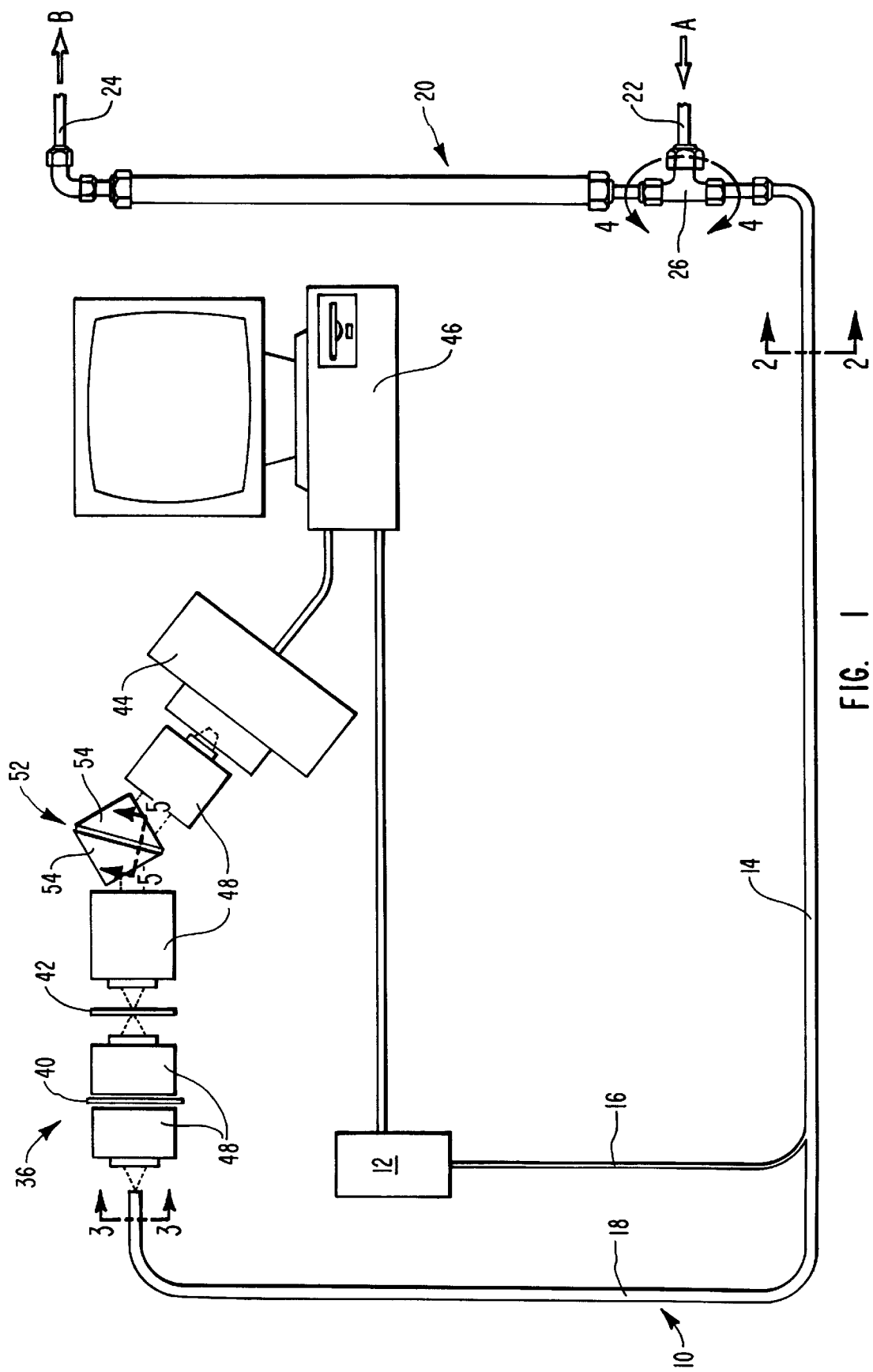
FIG. 1 is a schematic view of an apparatus for analyzing the composition of a fluid stream using Raman spectroscopy within the scope of the present invention.

Reference is now made to the figures wherein like parts are referred to by like numerals throughout. With particular reference to FIG. 1, a schematic representation of an apparatus 10 for analyzing the composition of a sample stream using Raman spectroscopy is illustrated.

The apparatus includes a laser source 12 for producing light having an excitation wavelength. Although conventional diode lasers can be used as the light source, it is presently preferred to use an external cavity diode laser. External cavity diode lasers can provide a more stable and higher power output signal than typical index guided single mode diode lasers. Currently preferred output power of the laser source is about 1 watt. The excitation wavelength is preferably in the range from 200 nm to 1550 nm. For analysis of petroleum products, the wavelength is preferably in the range from 450 nm to 1100 nm for use in Raman spectroscopy.

Figure 23:
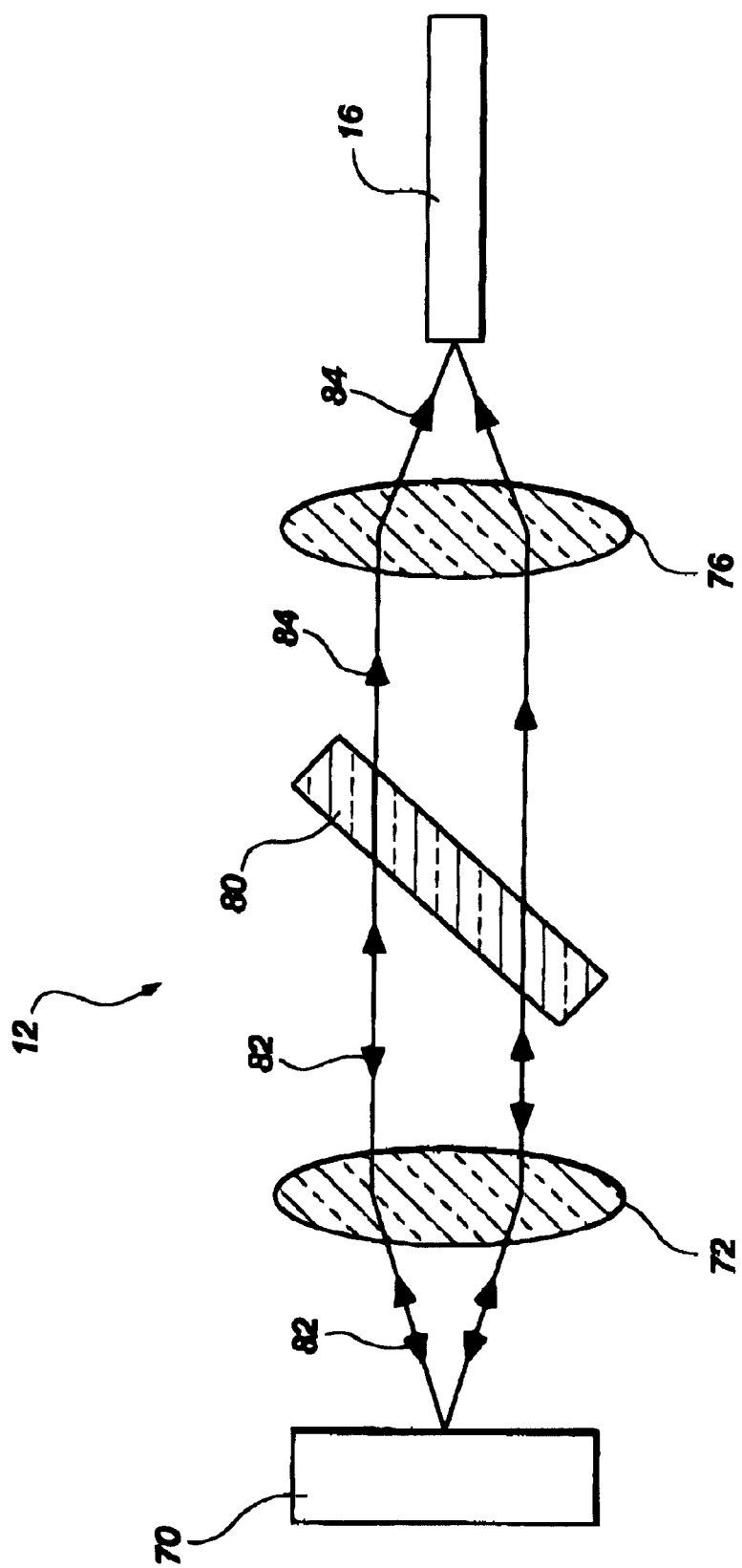
FIG. 23 is a schematic view of an external cavity laser within the scope of the present invention.

One currently preferred external cavity diode laser embodiment is shown in FIG. 23. The diode laser emitter 70 is preferably a commercially available broad stripe diode laser having a relatively large emitting area (100 $\mu$m×1 $\mu$m) and having a power of about 1 watt. The stripe size preferably ranges between 3 $\mu$m to about 500 $\mu$m. A plurality of diode laser emitters can be combined in an array to produce stripe sizes up to 1 cm. Larger stripe diode lasers generally produce more output power, but they are more difficult to couple to an optical fiber and produce a greater linewidth. Thus, the stripe size represents a balance between output power, efficient coupling to the optical fiber and adequate linewidth for the desired application. Several manufacturers sell diode lasers of this type, including Opto Power, Tucson, Ariz., Spectra Diode Laboratory, Inc., San Jose, Calif., and Coherent, Santa Clara, Calif. It will be appreciated by those skilled in the art that the diode laser emitter 70 can include an array of diode laser emitters assembled together.

These commercially available diode lasers come in a number of output wavelengths from 630 nm to 1550 nm, and preferably between 670 nm to 850 nm. Those skilled in the art of diode lasers will appreciate that the output wavelength can be as low as 450 nm and even 200 nm by selection of appropriate materials used to manufacture the diode laser emitter. The precise wavelength used in a spectrometer may vary depending on the material being analyzed. For liquids which tend to fluoresce, a higher wavelength, such as 850 nm, is preferred. For gas phase materials, shorter wavelengths, such as 670 nm or 788 nm, are preferred. Because Raman shifts further to the red (longer wavelengths) and gas phase materials have larger Raman shifts, a shorter wavelength is preferred so that the Raman shift does not exceed the detection limit of the CCD detector (usually about 1 $\mu$m).

The laser output is collimated with a collimating lens 72 and directed to a retro-reflection volume holographic grating 80 (R—R VHG). The R—R VHG 80 should have at least 600 grooves/mm and preferably between about 1200 and 2400 grooves/mm, and more preferably between about 1700 and 1900 grooves/mm. Light from the R—R VHG 80 passes through a focusing lens 76 which directs the light into the excitation fiber 16 of the bundle of optical fibers 14. The focusing lens 76 is preferably a single element lens to provide a compact design. However, a combination of lenses or prisms can be used to direct the light into the excitation fiber 16 more efficiently. It is also within the skill in the art to focus the light directly into a Raman sample cell, and thereby avoid the use of an excitation fiber 16.

The collimating lens 72 is preferably sufficiently large to capture the entire emission cone coming from the diode laser emitter 70. The light emission cone is typically about 40°, but can range from 300 to 450 depending on the structure and material of the diode laser emitter 70. The numerical aperture for the collimating lens 72 is preferably in the range from 0.5 to 0.6. The collimating lens 72 preferably has a long focal length, in the range from 8 mm to 10 mm. By having a long focal length, the diode laser emitter 70 can be spaced sufficiently from the collimating lens 72 so that the light source appears as a point source rather than a stripe. This allows the collimating lens 72 to distribute the light more uniformly onto the R—R VHG 80.

The R—R VHG 80 is preferably fully illuminated by the light coming from the collimating lens. The R—R VHG 80 resolution is improved by fully illuminating the grating. Increased diffraction grating resolution produces a narrower linewidth light output. The R—R VHG 80 groove orientation is preferably parallel to the diode laser emitter 70 stripe orientation to improve lasing and minimize the light output linewidth. The R—R VHG 80 directs light onto the focusing lens 76.

The focusing lens 76 preferably has a diameter large enough to receive all of the light coming off the diffraction grating 74. The focusing lens 76 preferably has a small numerical aperture in the range from 0.2 to 0.3. The numerical aperture preferably does not exceed the acceptance cone of the optical excitation fiber 16. The excitation fiber 16 can be a large diameter, multi-mode optical fiber to improve coupling between the focusing lens and the fiber.

A conventional Littrow grating retro-reflects at a wavelength where the angle of first order of diffraction equals the angle of reflection of a burnished or molded groove surface on the grating. Some diffraction gratings work in the first order and some, known as echelles and echellets, work only at higher orders and must be machined with great care to keep reflecting surfaces flat and smooth.

The R—R VHG 80 diffracts the first order light back to the laser for frequency stabilization (shown by arrows 82) and transmits the zeroth order light as output (shown by arrows 84). The R—R VHG works by diffracting in the first order at some wavelength in the direction perpendicular to the Bragg planes formed throughout the volume of the recording media. The difference between R—R VHG and conventional diffraction gratings is in how incident light is phase shifted and coupled in the reverse direction. The surface gratings of conventional diffraction gratings produce phase shifts by periodically providing equal path length differences in air, and the reflection is specular. The R—R VHG produces phase shifts with periodic changes in density in the plane of the substrate, and reflection is caused by coupling energy backward in a resonant multi-layer structure of much higher frequency periodic density changes through the volume of the material in a direction parallel to the plane of incidence.

The unique characteristics and advantages of using a volume holographic grating in the Littrow configuration are greater control over efficiency and bandwidth and the ability to completely encapsulate and protect the diffracting structure. These features allow the construction of a very rugged or robust grating that may be designed for bandwidths from as wide as a surface grating to as small as a few nanometers. Bandwidth and efficiency are controlled by film thickness and index or density modulation which are a function of exposure and processing. In addition, a design may be rapidly altered and tested both as a computer model and as a real device due to the intrinsically simple manner of construction with two coherent sources of collimated light.

Suitable R—R VHG devices can be obtained commercially from Ralcon Development Lab and Kaiser Optical. Many other commercial labs are equipped to make R—R VHGs on demand. The differences from lab to lab are related to materials used and the performance available from those materials. Currently, the best VHGs are made in dichromated gelatin (DCG) mainly due to the large dynamic range and low scatter of the material. Other suitable materials are photopolymers manufactured by DuPont and Polaroid.

The external cavity laser using a R—R VHG overcomes the drawbacks of conventional Littrow and Littman external-cavity lasers, but maintains their advantages. First, it is not necessary to reposition optics, such as the focusing lens, when the diode laser wavelength is changed as presently required with the Littrow external cavity laser when tuning the frequency. Second, it maintains compactness of the system by using only one optical element (a R—R VHG) instead of two elements (a traditional grating and a mirror) for a Littman external cavity laser. Third, the efficiency of the R—R VHG can be adjusted from a few percent up to 85 percent independent of the direction of the laser polarization. The diffraction efficiencies of traditional gratings are usually too low when p-polarization (parallel to grooves of the grating) is applied and the incident angle is large. Fourth, the system is much simpler because all optical components are on a straight optical axis. Fifth, R—R VHGs can be easily assembled, cleaned, and handled because the grating material is protected by two thin pieces of glass. The external cavity design can be used with laser array, narrow stripe, or broad stripe diode laser devices.

It is currently preferred to construct the external cavity diode laser with the components coupled with Invar material. Invar is a nickel-iron alloy having a low coefficient of thermal expansion. Invar coupling provides stable alignment of the diode laser components over a range of temperatures.

The light from the laser source has a typical linewidth of between 20 and 50 GHz and preferably less than 30 GHz. For many applications, such as analysis of liquid petrochemicals, a linewidth as high as 120 GHz can be used, although a linewidth between 20 and 30 GHz is usually preferred. For analysis of gas phase components, a linewidth as high as 300 GHz can be used, and the number of grooves in the diffraction grating 74 can be reduced to about 600 grooves/mm.

Figure 24:
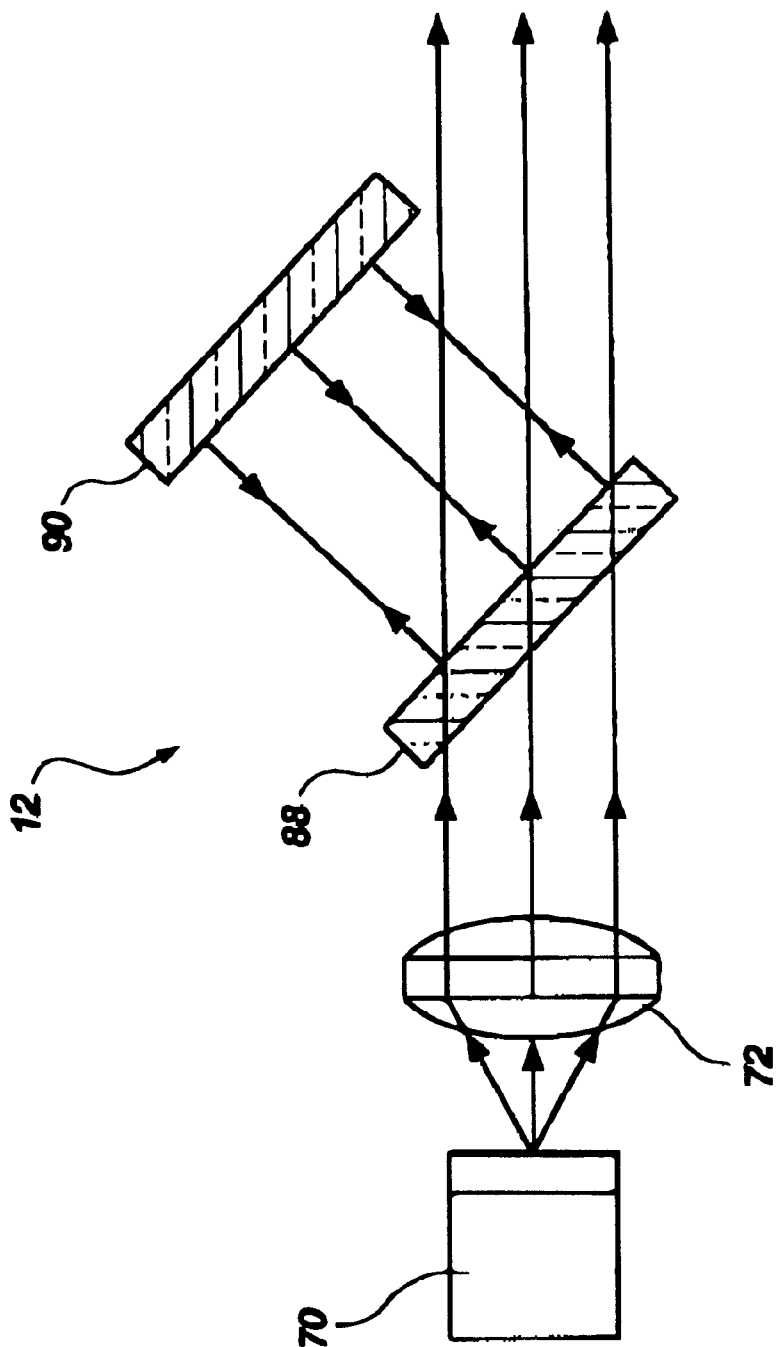
FIG. 24 is a schematic view of another external cavity laser within the scope of the present invention.

Another external cavity diode laser embodiment is illustrated in FIG. 24. The external cavity diode laser 12, shown in FIG. 24 includes a diode laser emitter 70 and a collimating lens 72. Although not shown, a focusing lens for coupling the output to an excitation optical fiber can be used in the manner described above. The diode laser emitter 70, collimating lens 72, focusing lens, and fiber have the characteristics and functions described above. Instead of using a diffraction grating, such as those used in conventional Littman external cavity diode laser systems, the external cavity diode laser of FIG. 24 includes a volume holographic transmission grating 88 (VHTG). A high reflectivity mirror 90 (>99%) is provided according to traditional Littman configurations.

The external-cavity construction shown in FIG. 24 is an extension of a design commonly used for low-power External-Cavity Semiconductor Lasers (ECL). The system preferably includes a 1 Watt (788 nm) BAL, a 4.5 mm focal-length collimating lens (N.A.=0.55), a 900 grooves/mm Volume Holographic Transmission Grating (VHTC) (0.5"33 1") 88, and a high reflectivity (>99%) mirror 90. These four elements are preferably positioned on an aluminum base plate (3/8" thick) that is temperature controlled at 20° C. with a stability better than 0.01° C. The cavity length is about 5 cm and the grooves of the grating are parallel to the p-n junction of the BAL.

One major difference between the ECL shown in FIG. 24 and a traditional Littman ECL is that the system disclosed in FIG. 24 uses a special VHTG, rather than an ordinary reflection grating, which allows better efficiency for the p-plane polarized light and is more compact. In addition, VHTGs are much easier to maintain and handle since the grating material is sandwiched and protected by two thin pieces of glass. The first-order grating efficiency is measured to be about 60% at an incident angle of 22°. The effective optical feedback to the laser is thus estimated to be about 18% assuming a coupling loss of 3 dB from the collimating lens.

For the Littman configuration of ECLs, the theoretical double-passband of the grating is about 19 GHz assuming a wavelength of 788 nm, a grating density of 900 grooves/mm, and a beam radius of 2.5 mm. The measured total output-power efficiency (compared to free-running optical power) is only about 20% because the protective glass of the VHTG is not anti-reflection coated. The dimensions of the whole system without electronics are about 9 cm×8 cm×7 cm (L×W×H). Finally, tuning is achieved by rotating the mirror (not grating), resulting in an unsteered output beam.

Figure 25:
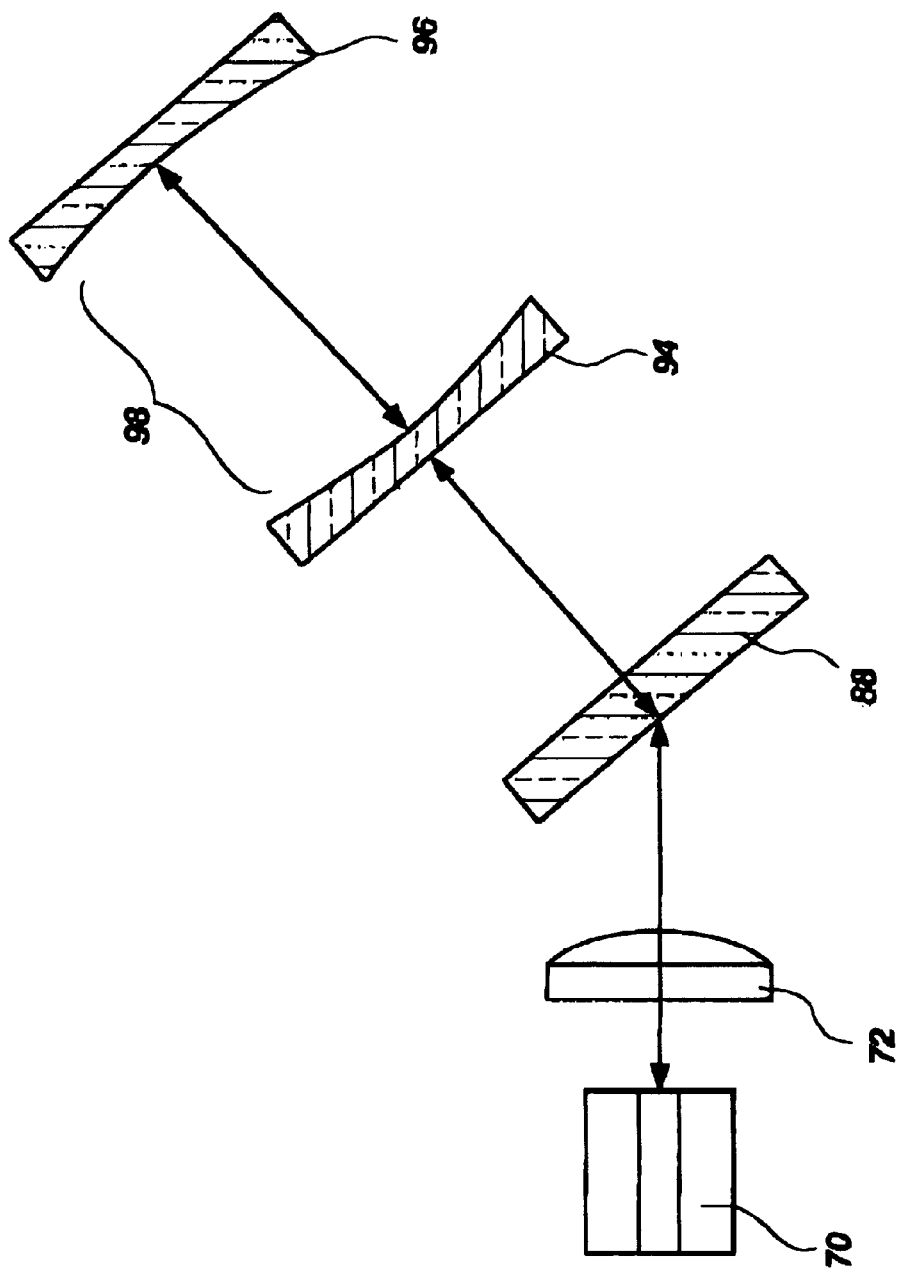
FIG. 25 is a schematic view of another external cavity laser within the scope of the present invention having a power buildup cavity useful in analyzing gaseous samples.

Yet another external cavity diode laser embodiment is illustrated in FIG. 25. The system shown in FIG. 25 contains a low-Q, high-power buildup cavity which is particularly useful in analyzing gaseous samples. The external cavity diode laser 12, shown in FIG. 25 includes a diode laser emitter 70, a mode matching collimating lens 72, and a volume holographic transmission grating 88 (VHTG) similar to the system illustrated in FIG. 24. The diode laser emitter 70, collimating lens 72, and VHTG 88 have the characteristics and functions described above. Two mirrors 94 and 96 perform the same function as the mirror 90 shown in FIG. 24. However, the space between mirrors 94 and 96 defines a power buildup cavity 98.

The use of power buildup cavities in Littman-type external cavity laser systems is known from U.S. Pat. No. 5,642,375 to King et al. However, the system shown in FIG. 25 has many advantages over the King et al. system, including narrower bandwidth and improved long-term stability. From a practical point of view, because King et al. discloses a high-Q system, it looses its buildup power easily due to contamination on the optics. The system in FIG. 25, includes a volume holographic transmission grating located between the mode matching lens 72 and the power buildup cavity 98 to suppress the bandwidth of the system for gas-phase Raman spectroscopy. The two mirrors 94, 96 forming the power buildup cavity can be thought of as an effective mirror that is similar to the external mirror 90 used for the tuning mirror in the embodiment shown in FIG. 24. Contamination of the power buildup cavity 98 can be avoided by using a brewster angled sample cell inside the buildup cavity.

A typical bandwidth of the grating passband around 100–200 GHz is sufficient. The VHTG 88 prefers to have high efficiency about 85% and about 1800 lines per millimeter. The laser diode 70 is intended to increase the input power to the buildup cavity while lower the Q of the cavity. A typical 500 mW (100 microns stripe width) laser diode at 660 nm can be used. It is only necessary to mode match the cavity in the near gaussian beam direction of the laser diode 70 for better mode-match efficiency. When the external cavity laser diode of FIG. 25 is used in a Raman spectrometer, it is possible to excite a multimode pattern along the multimode direction of the laser diode 70 because the collection optics and the slit of the spectrograph only "see" a narrow beam along near gaussian beam direction. If the system needs 10 Watts of pumping power, a gain of only 20 for a 500 mW laser is needed, assuming 100% mode-matching efficiency. Thus, the system of FIG. 25 is far more stable than the high-Q system disclosed in King et al.

Figure 2:
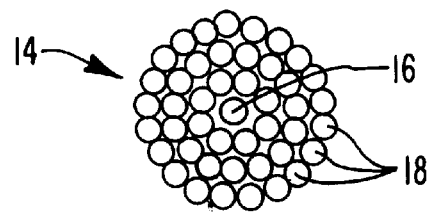
FIG. 2 is a cross sectional view of a bundle of optical fibers used to transmit light having an excitation wavelength and to receive scattered light.

The output light from the external cavity diode laser system is preferably introduced into an excitation optical fiber 16 which is combined with one or more collection optical fibers 18 to form a bundle of optical fibers 14. One currently preferred optical fiber bundle 14 configuration is illustrated in FIG. 2. Such optical fiber bundles are commercially available from manufacturers such as Fiberguide Industries, Inc., Stirling, N.J. The fiber bundles preferably contain at least 30 or more fibers, and more preferably from 40 to 50 fibers. The individual fibers have a small size to maintain good spectral resolution. optical fibers having a diameter in the range from about 4 $\mu$m or 5 $\mu$m and up to about 1 mm can be used, with the presently preferred size being between 50 $\mu$m to 500 $\mu$m. If the fibers are between 10 $\mu$m and 25 $\mu$m, then it may be possible to avoid using a slit in the Raman spectrometer by aligning the exit ends of the collection fibers in a linear array. Typically, only one fiber is required as the excitation optical fiber, although it is possible to use more that one fiber to carry the excitation light. The remaining optical fibers are collection optical fibers to receive backscattered Raman signal (light).

Figure 4:
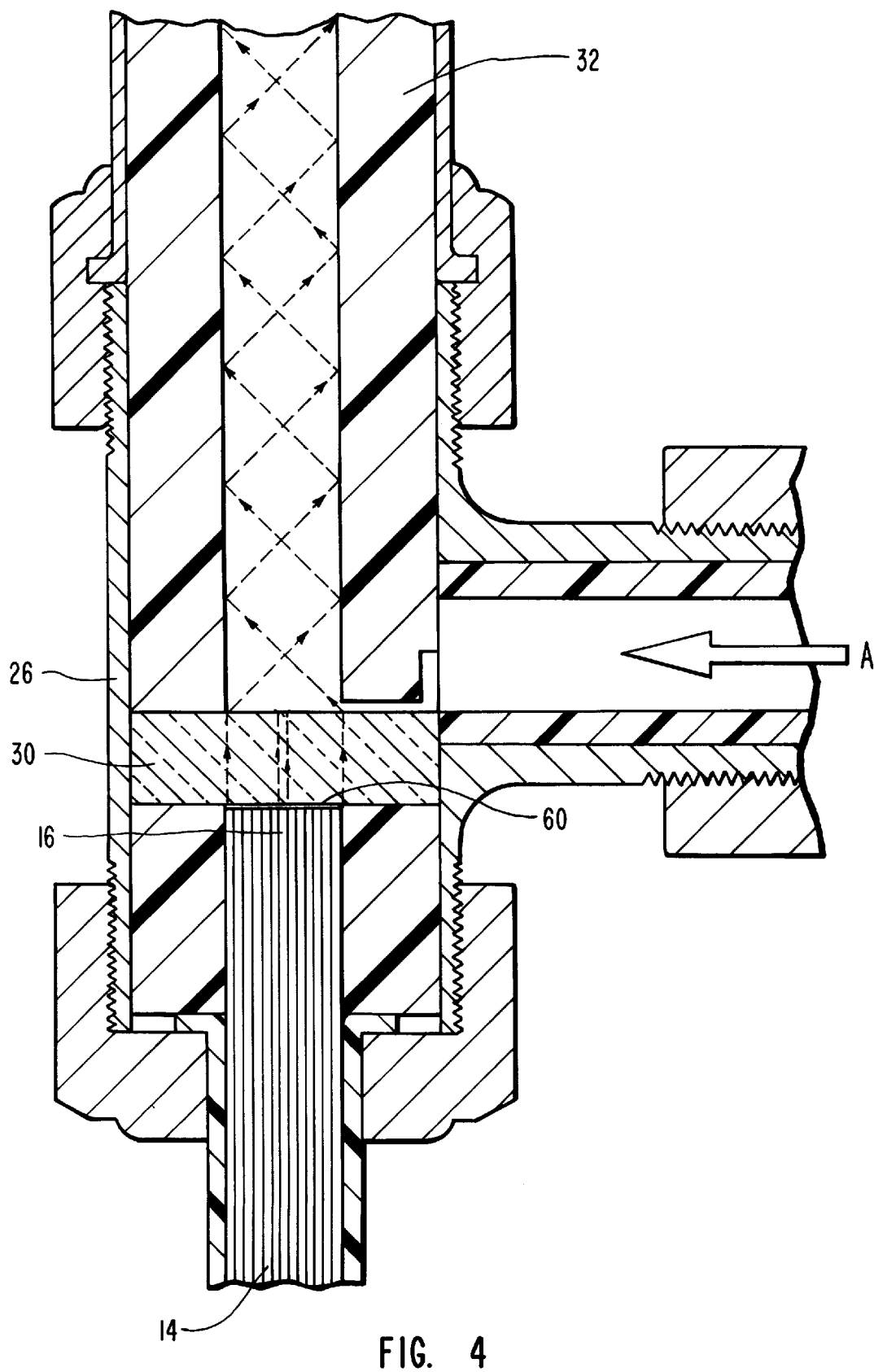
FIG. 4 is an enlarged cross sectional view of one end of a Raman sample cell showing connection of an optical fiber bundle and fluid entrance into the sample cell.
Figure 22:
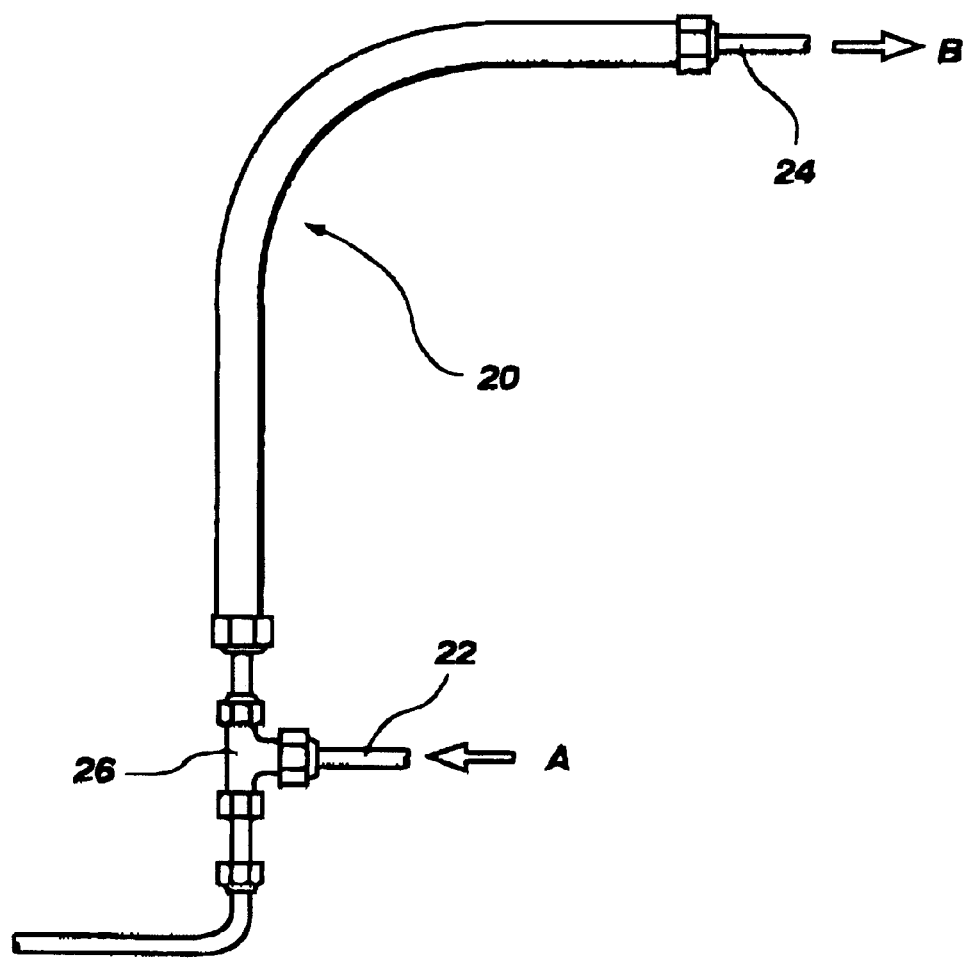
FIG. 22 is a view of a Raman sample cell in a curved orientation between the sample stream inlet and the sample stream outlet.
Figure 26:
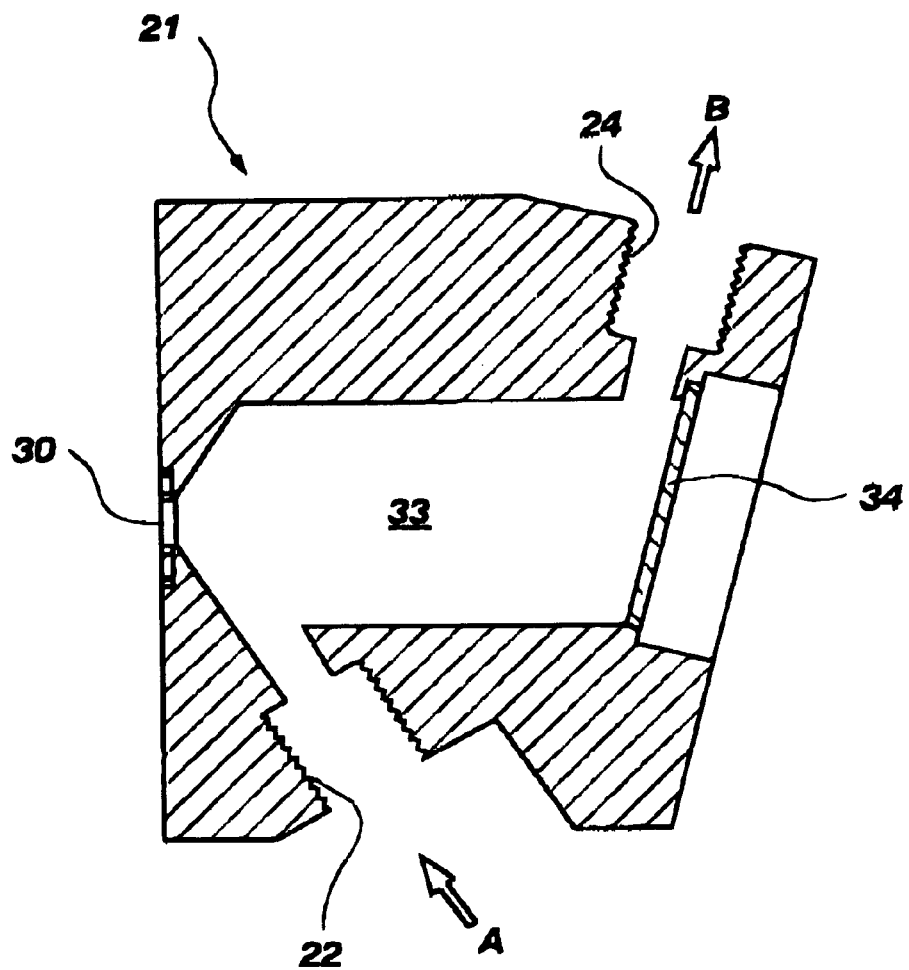
FIG. 26 is a cross-section view of a flow-through Raman sample cell.

The fiber bundle is optically connected to a Raman sample cell. One possible Raman sample cell 20 is shown in FIGS. 1, 4, and 22. Another presently preferred Raman sample cell 21 is shown in FIG. 26. The Raman sample cell 20, of FIGS. 2, 4, and 22 is preferably configured to allow continuous sample flow therethrough, illustrated by arrows A and B. A sample stream inlet 22 and a sample stream outlet 24 are located adjacent the ends of the sample cell 20 to allow sample flow through the sample cell 20. Experimental tests indicate that the sample flow rate does not affect the Raman spectroscopy results and sample flow can go in either direction. An optical connector 26 located at one end of the sample cell permits connection of the optical fiber bundle 14 to the sample cell 20.

As shown best in FIG. 4, the Raman sample cell 20 preferably includes the close coupling of the adjacent bundle of optical fibers 14 to couple the light from the excitation optical fiber 16 into the sample cell 20 and to allow back-scattered Raman light from the sample cell to enter the one or more collection optical fibers 18. A optional transparent barrier 30 is preferably located between the bundle of optical fibers 14 and the sample flow (shown by arrow A) within the sample cell 20. An index matching fluid 60 is put between the fiber bundle tip and the barrier to improve optical coupling efficiency. Suitable index matching fluids are commercially available. They are typically clear viscous fluids, such as mineral oil or glycerol, which fill any voids between two optical surfaces. Optical epoxy can also be used, but it would result in permanent attachment of the fiber bundle to the sample barrier.

The Raman sample cell 20 is preferably lined with a waveguide core (liner) 32 having an index of refraction less than the index of refraction of the sample stream. If the index of refraction of the liner is low enough, much of the light will reflect internally at the interface between the fluid sample and the sample cell liner 32, as shown in FIG. 4. Of course, the sample cell can be lined with a transparent material, such as glass, which will cause reflection to occur at the exterior surface of the liner. Because light loses some of its intensity as it passes through the liner, it is presently preferred to line the sample cell with a low index of refraction material. Fluorinated polymers, such as polytetrafluoroethylene (PTFE), PFA, copolymer of tetrafluoroethylene and hexafluoropropylene (FEP), AF and Tefzel, are currently preferred because they have indexes of refraction from below about 1.29 to 1.35. Preferred index of refraction is one that is less than the sample being analyzed. The enhancement factor for the cell is dependent upon the refractive index of the sample solution in the cell. Different solution refractive indices result in different critical angles and different effective sample path lengths.

The length and width of the Raman sample cell 20 can vary. Generally, a longer sample cell will yield a larger enhancement effect up to the point where additional cell length will have less and less effect because of internal losses in the liquid medium and the waveguide core. The Raman sample cell 20 preferably has a length in the range from about 0.1 m to about 4 m, with a preferred length ranging from 1 to 2 meter, depending upon the degree of sensitivity desired. A sample cell length of one to two meters yields excellent amplification of the Raman signal while still being easy to fabricate and install.

The sample cell preferably has a diameter in the range from about 0.005 to 0.2 inches. For any given cell length, the smaller the waveguide diameter, the greater the enhancement effect. The preferred diameter is determined more by what size waveguide is the easiest to fabricate and produce and to what extent the Raman signal needs to be enhanced. A presently preferred diameter is about 0.03 inches, mainly because of the ease of fabrication and the ability to maintain a reasonable level of flow. Too small a diameter, such as 0.005 inches, will yield excellent Raman signal enhancement, but the pressure required to obtain a reasonable flow through the cell will be high. Too large of a diameter, i.e., greater than 0.2 inches, will greatly reduce the Raman signal enhancement effect for a practical length of waveguide.

The Raman sample cell 20 may be rigid or flexible. In operation, acceptable performance is obtained with the sample cell in either linear, curved or coiled configurations. One representation of a curved Raman sample cell is shown in FIG. 22. If the sample cell is coiled, it is preferred to maintain the bend radius greater than ½ inch to minimize signal loss caused by bending the waveguide.

FIG. 26 illustrates another preferred Raman sample cell 21. The sample cell 21 includes a sample stream inlet 22 and a sample stream outlet 24. Laser light enters the sample cell 21 through a transparent barrier 30 and interacts with the sample within the sample volume 33. An absorption filter 34 which absorbs light having the excitation wavelength is located opposite the transparent barrier 30. The absorption filter 34 is placed at an angle to minimize the amount of reflected light which can pass into the one or more collection fibers. The sample cell 21 is not very flow dependent, and it can be made with any practical internal volume. It is currently preferred to have the internal volume range from about 1 cc to about 20 cc. The longer the sample cell 21, measured between the transparent window 30 and the absorption filter 34, the more Raman interaction and consequently the greater the Raman scattered light to be received by the one or more collection optical fibers.

Figure 3:
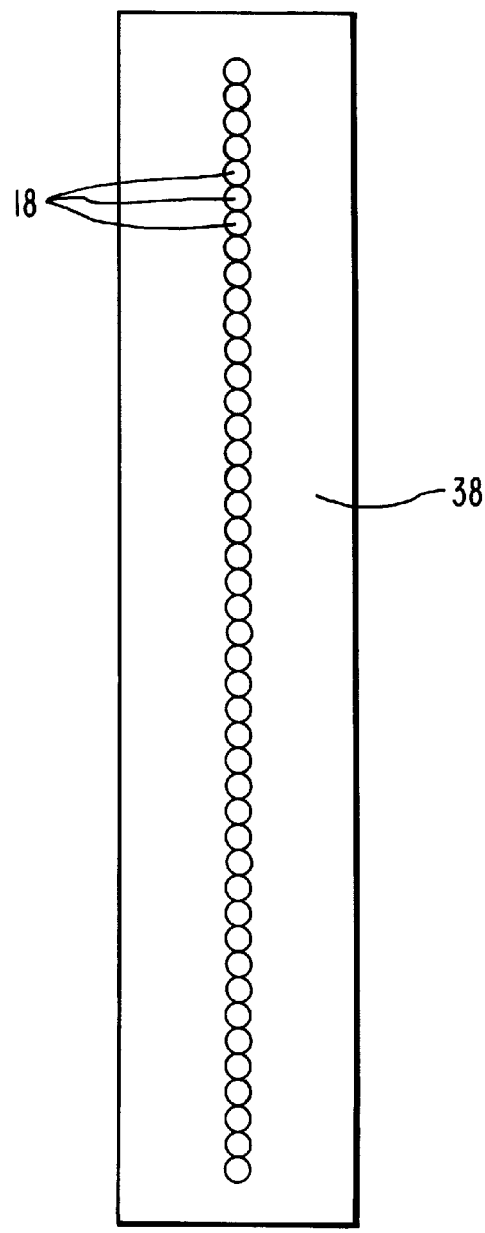
FIG. 3 is a cross sectional view of the linear array of collection optical fibers.

In use, scattered light from the sample cell enters the one or more collection fibers for transmission to a Raman spectrometer 36. As shown in FIG. 3, the exit end of the collection fibers is preferably aligned in a linear array 38 so that a linear optical signal is generated. The Raman spectrometer 36 passes the linear optical signal through a filter 40 to eliminate portions of the optical signal having the excitation wavelength. A suitable filter must have good laser line rejection, such as a holographic or dielectric filter. Suitable dielectric filters are manufactured by optical filter companies such as Omega Optical. The holographic filter is made by companies such as Kaiser Optical, Ann Arbor, Mich. and Ralcon Development, Paradise, Utah.

The optical signal is also passed through an optical slit 42 to remove stray light. The optical slit 42 typically has dimensions comparable to the width and height of the linear array 38 of collection optical fibers. The narrower the slit the better the spectral resolution. However, this increased resolution also reduces the overall signal throughput. The optical slit preferably has a width in the range from 10 microns to 150 microns. In a currently preferred embodiment, the slit ranges from 7 mm×25 $\mu$m to 7 mm×100 $\mu$m. A linear array of optical fibers can perform the same function as the optical slit by generating a linear optical signal. In this manner, the slit and associated optics can be replaced by the linear array of optical fibers.

A commercially available charge coupled device ("CCD") 44 converts the optical signal into a corresponding electronic signal to be analyzed by a computer 46 and converted into a representation of the chemical analysis of the fluid stream. The computer 46 can also be used to control the laser source 12.

A plurality of optical lenses 48 are provided to receive and convey the optical signal from the linear array 38, through the Raman spectrometer 36, to the charge coupled device 44. The speed of the optical lenses can vary, but faster speeds are generally preferred in order to capture more light. The improved performance obtained by faster lenses must be balanced by the increased cost of the lenses. Optical lenses having a speed in the range from f/1.0 to f/2.8 have been found to be suitable, although lens speed outside this range can be used.

Figure 5:
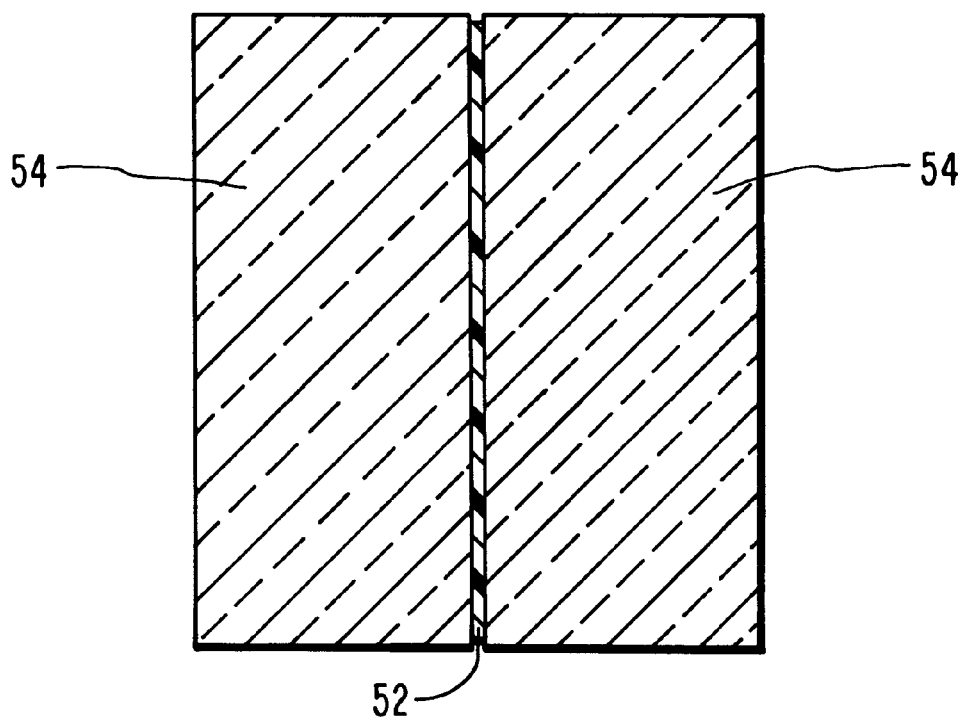
FIG. 5 is a cross sectional view of an aberration correction element and volume holographic grating within the scope of the present invention.

A volume holographic transmission grating 52 is used to disperse the signal. If necessary, the focusing function of the optical lenses can be performed with the volume holographic grating. An aberration correction element 54 is preferably provided to correct optical aberrations introduced into the optical signal by the volume holographic grating 52. One presently preferred aberration correction element 54, illustrated in FIG. 5, is a pair of 450 right-angle prisms 54. Other optically transparent components such as wedges can be used for aberration correction. The aberration correction elements could be joined together and placed in front of or behind the holographic grating element. It is important that the aberration correction element contain a sufficient thickness of optically transparent material to correct the aberrations produced by the volume holographic transmission grating.

The configuration shown in FIGS. 1 and 5 is currently preferred because it requires less space and allows the closer coupling of the optical elements, i.e. the grating, lenses, and CCD array. It also allows for the use of higher resolution gratings. The closer coupling allows for greater light throughput for any given lens size.

The volume holographic transmission grating 52 can be fabricated with various degrees of spectral resolution with equivalent grooves/mm from several hundred grooves/mm up to 2400 grooves/mm. The preferred resolution is on the order of 1500 grooves/mm to 2400 grooves/mm. More grooves per mm increases the spectral resolution, but also decreases the optical signal throughput. Increased spectral resolution also increases the aberration that must be removed to obtain improved resolution. The choice of grating resolution depends upon the resolution required, the range covered by the CCD detector, and the degree of signal throughput desired. The volume holographic transmission grating 52 is preferably sandwiched between the two optically transparent aberration correction elements 54.

The volume holographic grating 52 is used because of its high efficiency in dispersing light into the needed spectrum and also because it can be used with very fast optical lenses. Overall signal throughput is increased by several orders of magnitude compared with conventional spectrometers using conventional reflective optics and gratings. This increased efficiency allows for enhanced sensitivity in detection of Raman signal and greater speed of detection. A currently preferred volume holographic transmission grating is commercially available from Kaiser Optical Systems, Ann Arbor, Mich. or Ralcon Labs, Paradise, Utah. The prisms, optical lenses and all optical interfaces are preferably coated with anti-reflection coatings to minimize light losses through the spectrometer.

For Raman spectrometers which include fiber-optic coupling of the Raman signal to the spectrometer, the volume holographic transmission grating 52 is preferably designed for optimum efficiency with the randomly polarized light carried by the optical fiber bundle 14. The grating is preferably designed to balance the diffraction efficiency for the "s" and "p" polarization modes. This allows the grating to pass more Raman signal when confronted with a randomly polarized signal. Most holographic gratings are not designed to work efficiently in the near infrared region. Refractive index modulation in the grating is preferably optimized for near infrared operation. The emulsion thickness of the grating 52 is preferably designed thinner to obtain a flatter diffraction efficiency curve over the near infrared spectral region (840 to 950 nm).

The prisms 54 have another function in addition to correcting signal aberration caused by the volume holographic transmission grating 52. When the grating is sandwiched between two optical wedges (prisms), the grating can operate at higher effective groove densities and provide higher spectral resolution. The sandwiched prism design allows the holographic transmission grating 52 to have a grating resolution greater than 2300 grooves/mm. Normally, holographic transmission gratings operating in air alone have a practical resolution limit on the order of 1700 grooves/mm. The increase in resolution afforded by the disclosed design offers improved signal throughput for faster integration times and improved Raman signal resolution. Raman peaks that are very close together (resolution of 4.5 $cm^{-1}$) can be effectively detected and measured according to the disclosed design.

Several experiments were performed using a Raman spectroscopy apparatus as shown in FIG. 1 to analyze various petroleum products. The results of these tests are illustrated in FIGS. 6–18. The sample cell had a length between 0.31 and 2 meters and a diameter between 0.06 and 0.03 inches. A diode laser generating an excitation wavelength between 780 and 800 nm was used. The diode laser had a power output between 50 and 100 mW. The integration times ranged from 60 to 90 seconds.

Figure 19:
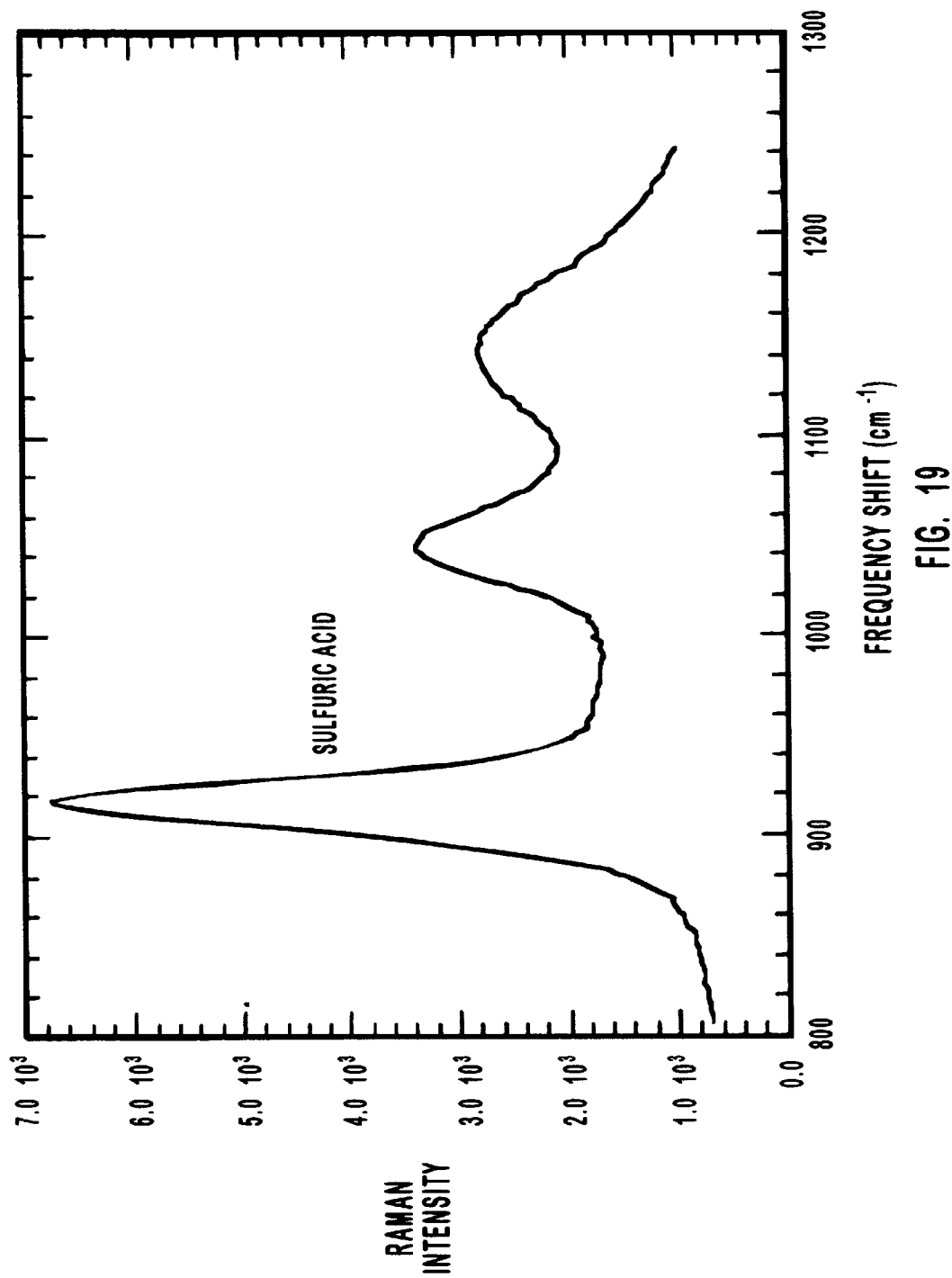
FIG. 19 is a graph of the Raman spectrum for pure sulfuric acid, with a major Raman peak at 920 $cm^{-1}$.
Figure 20:
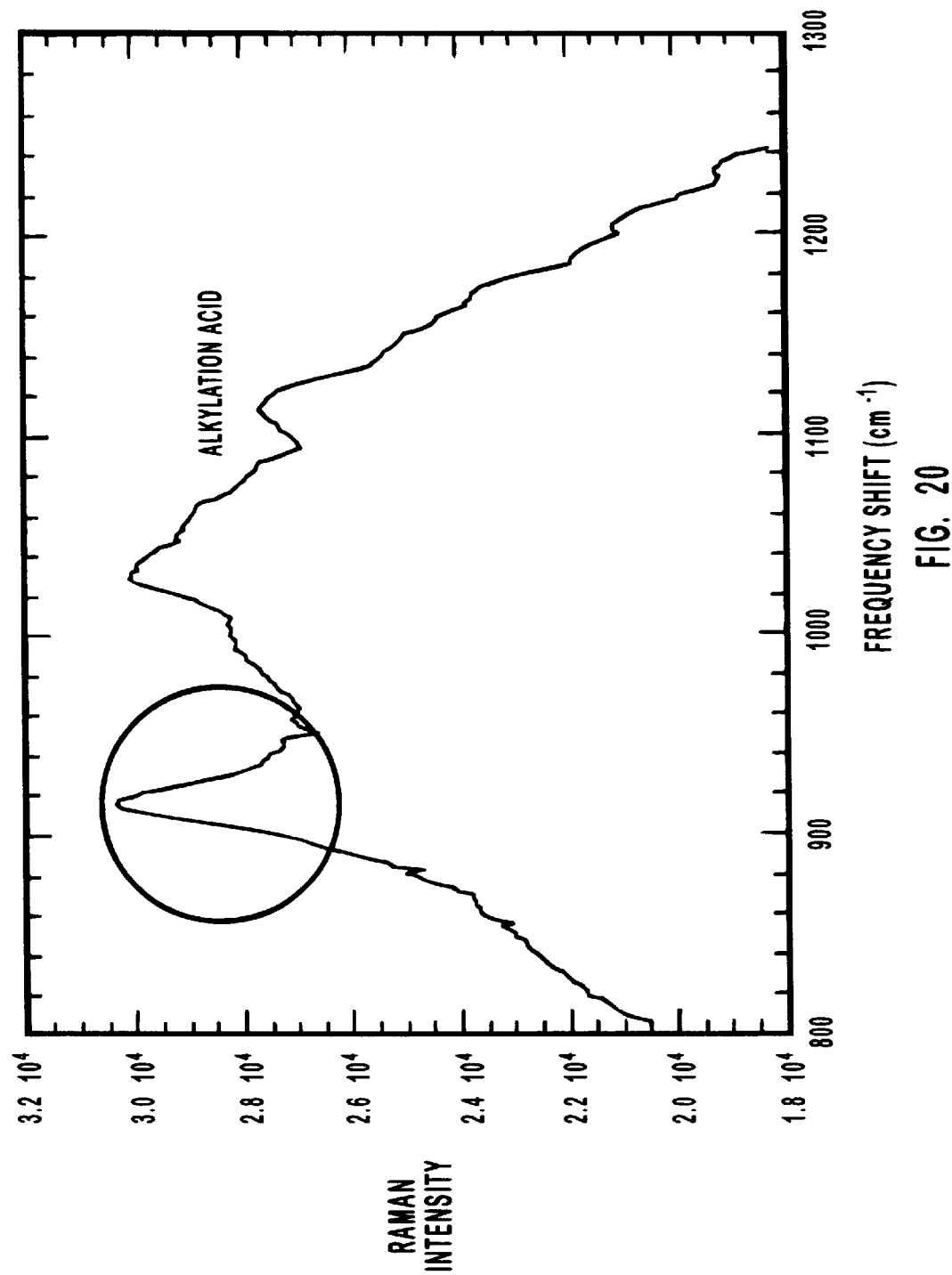
FIG. 20 is a graph of the Raman spectrum showing the sulfuric acid Raman peak present in a sample of alkylation acid.
Figure 21:
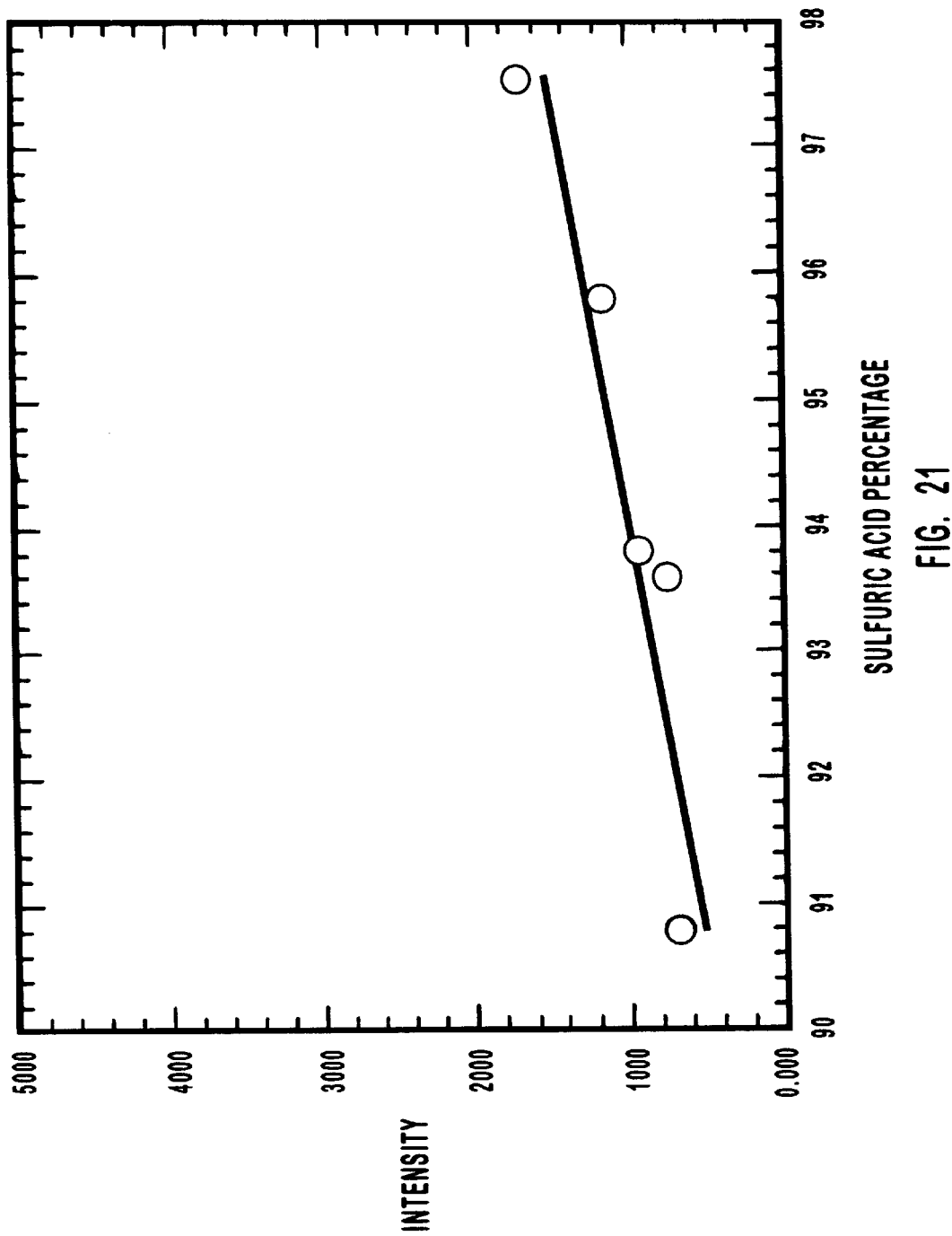
FIG. 21 is a graph of Raman intensity versus acid percentage indicating a linear relationship between the Raman signal strength and the actual acid concentration in the alkylation acid process stream.

Additional experiments were performed to analyze sulfuric acid and process streams containing sulfuric acid. The results of these tests are illustrated in FIGS. 19–21. The Raman spectroscopy apparatus was identical to that described above, except that an excitation wavelength of 847 nm was used.

Octane Determination

Figure 6:
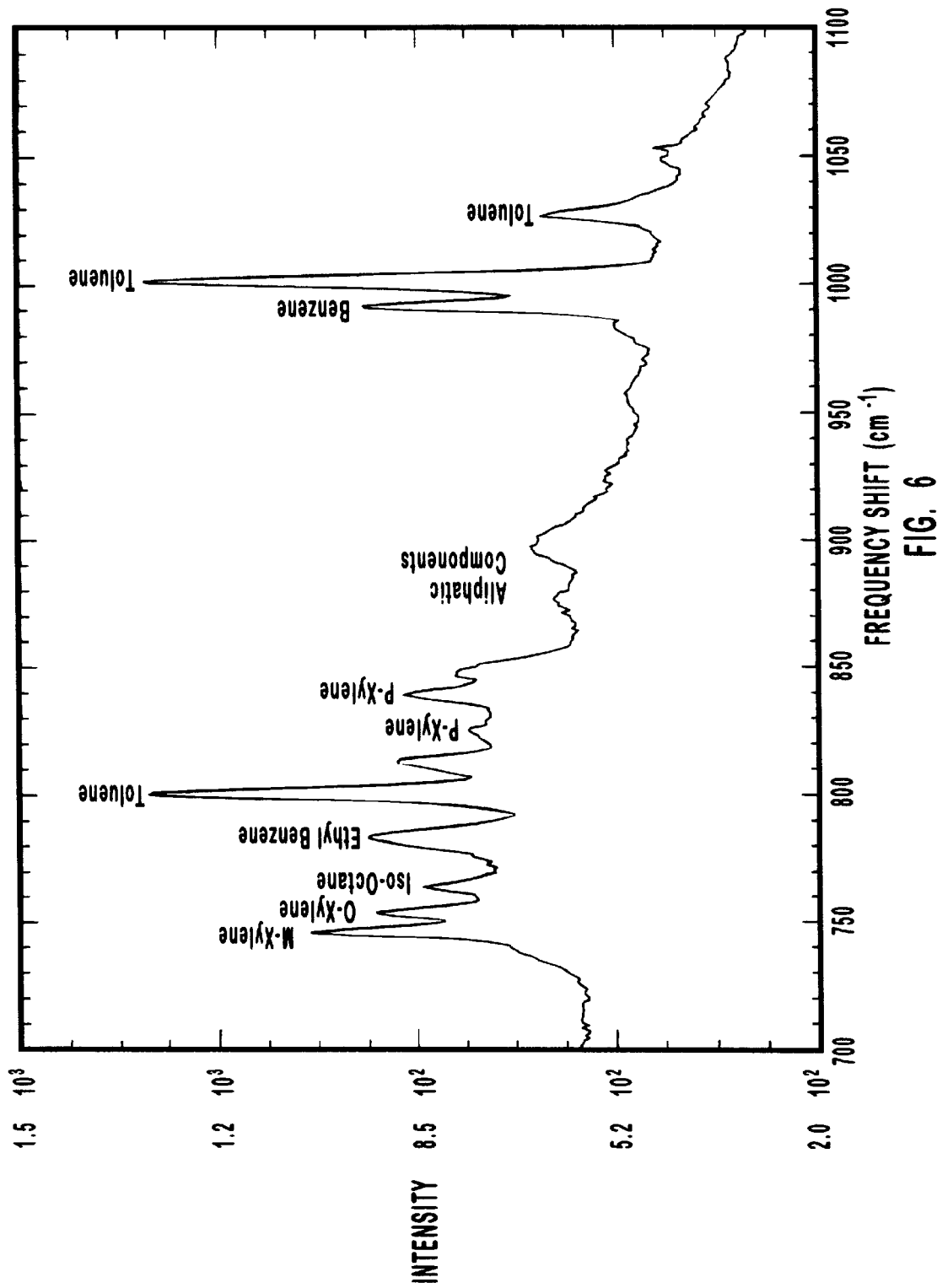
FIG. 6 is a graph of the Raman spectrum of unleaded gasoline obtained with an apparatus according to the present invention.

FIG. 6 identifies the location and relative intensities of the Raman peaks for the major constituents of gasoline. Toluene, m-, o-, and p-xylene, ethyl benzene, and benzene make up most of the important aromatic constituents. Isooctane is a major ingredient whose concentration can be adjusted to readily increase or decrease octane rating. The aliphatics, such as n-heptane and n-hexane, have Raman peaks that are much broader than the aromatics, and their peaks are illustrated in the region from 890 to 940 $cm^{-1}$. By measuring the relative intensities of the "octane enhancers" such as m-, o- and pxylene, isooctane, ethyl benzene and toluene to the intensities of the aliphatics, one can develop a model that will determine the octane rating of the fuel. It is necessary to be able to distinguish these compounds from the aliphatics that reduce octane ratings rather than increase the octane rating. The aromatics and isooctane tend to be the most important compounds in determining octane rating and their Raman peaks are very narrow and distinct in this "finger print" region of the frequency scale, i.e., 700 to 1025 $cm^{-1}$.

Commercially available chemometric analysis software such as MATLAB, sold by The Math Works, Inc., Natick, Mass., or GRAMS/386, sold by Galactic Industries Corporation, Salem, N.H., can be used to develop the octane rating model. The combustion properties reflected in octane number can be derived from a variety of compositions of branched and aromatic hydrocarbons. Thus, the calibration model development must include a full spectrum analysis to capture the range of structures that relate to octane number. Since the composition of fuels can vary considerably, the algorithm must have robust predictive capabilities. For this task, it is currently preferred to first use the principal component regression approach of partial least squares or "PLS." This approach extracts a set of factors that capture the variation in the calibration spectra that relate to variation in the property being predicted while ignoring variation that is not related to this property. This attribute of PLS allows for a wider variation in compositions of unknowns that could be tolerated in classical least squares or more traditional principal component regression approaches.

Model development and calibration will proceed using standard samples which have been octane graded by standard knock engine techniques; samples from a variety of refineries will be brought into the calibration set. Cross-validation (leaving out the standard being tested) should be used to check the predictive capabilities of the model over the calibration set; many tests of the model and method should be performed during instrument calibration while operating online, in parallel with a knock engine. Continuous quality testing of the model is carried out during analysis; lack-of-fit criteria testing of the model is carried out during analysis; lack-of-fit criteria (excess spectral error, structured residuals) are examined for all unknown samples with outliers preferably stored for further evaluation. Once the model is developed and tested, suitable analysis software is developed based on the model.

Figure 7:
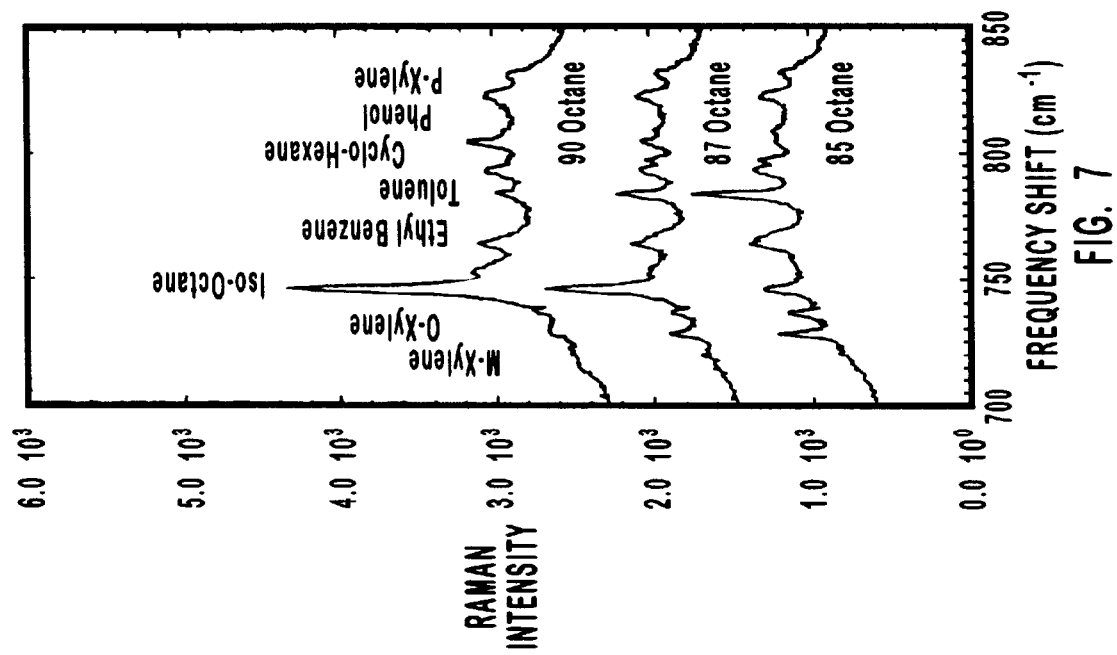
FIG. 7 is a graph of the Raman spectrum of various octane grades of gasoline fuel showing the changes in the key octane determinant peaks as the octane rating changes.
Figure 11:
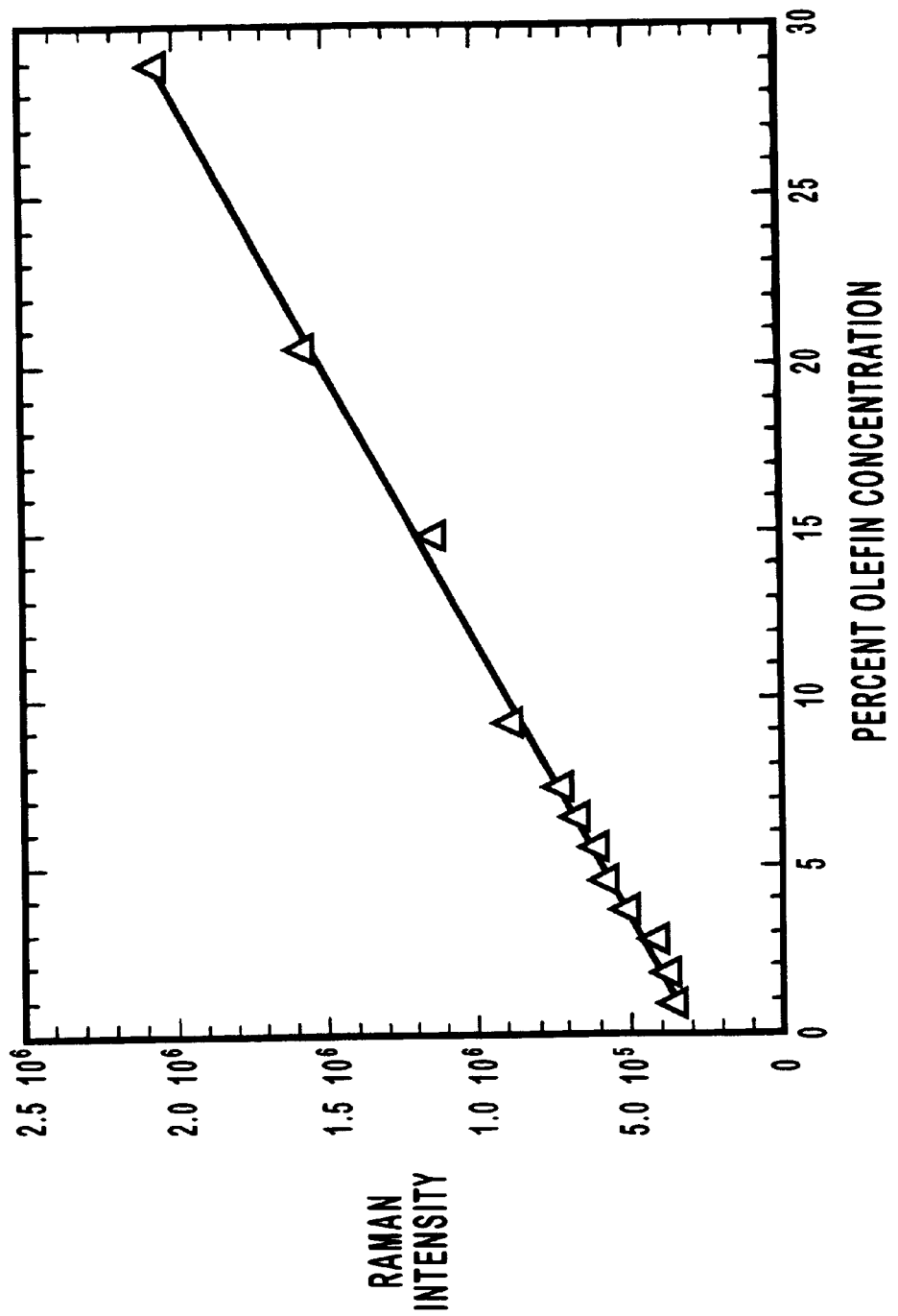
FIG. 11 is a graph of Raman intensity versus total olefin concentration for the curves shown in FIG. 10, indicating a linear relationship between Raman signal strength and the total olefin concentration.

FIG. 7 illustrates how Raman measurements can identify the changes in the key octane determinant peaks as the octane rating changes in fuel. With higher octane rating the octane enhancer isooctane increases in concentration, while toluene concentration decreases. Each petroleum company has its own special blending practices to produce their higher octane rated gasolines. The Raman spectra need to be generated for each company's gasoline and that information put into a mathematical model that can then be used to determine the octane rating for that refiner's products. A model for one company's fuel system may or may not work directly for another fuel system. The models may have to be made individually for each blending pattern.

Figure 8:
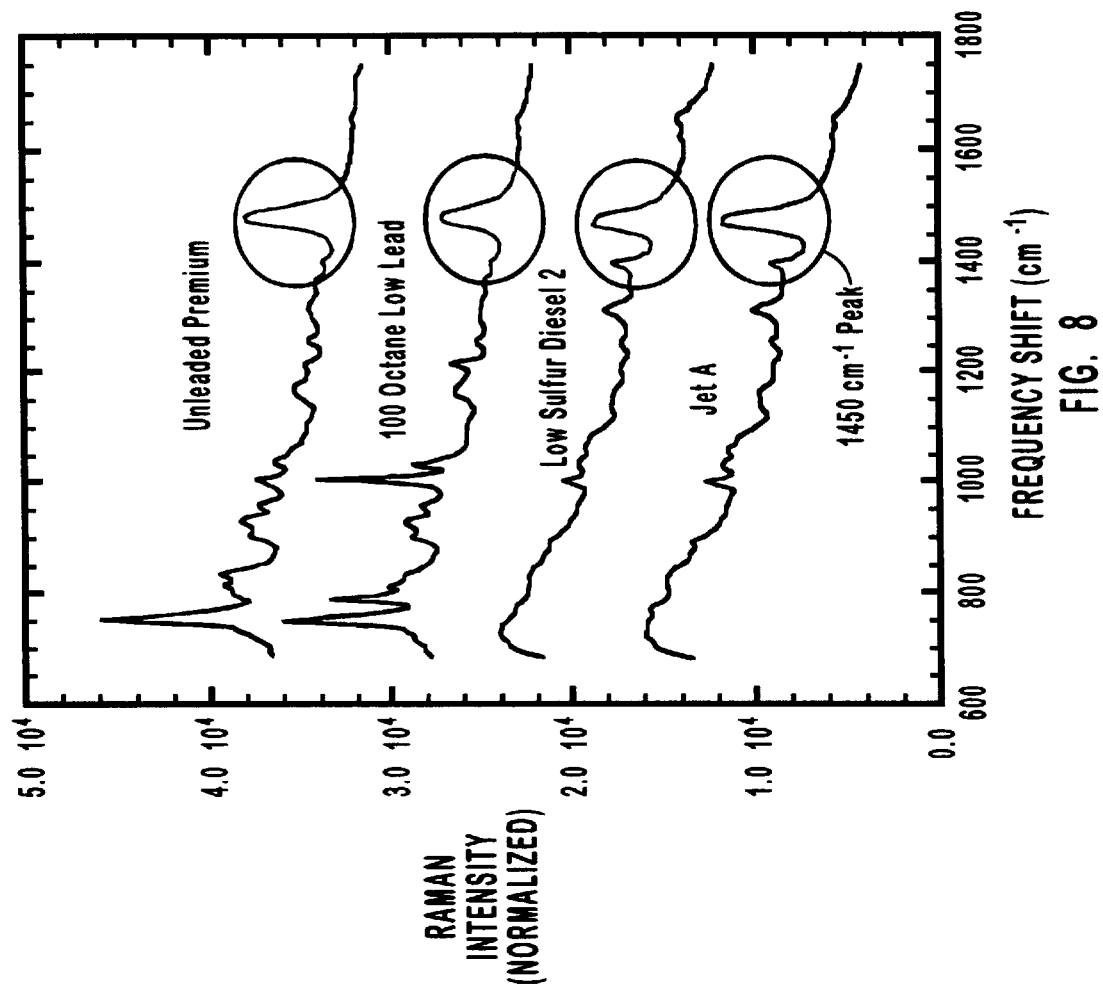
FIG. 8 is a graph of the Raman spectrum around 1400 $cm^{-1}$ and 1440 $cm^{-1}$ of different types of fuels which can be used to indicate change in the laser power.

FIG. 8 illustrates the existence of Raman peaks in the Raman spectrum around 1400 and 1440 $cm^{-1}$ that change very little with different types of fuels as well as with different octane ratings. These peaks are made up of the Raman spectra of many of the gasoline components, thus these peaks stay relatively constant with changing individual gasoline constituents. Although these peaks are not useful for analyzing a particular aliphatic or aromatic component, they can be used as an internal reference to ensure that the relative excitation energy has not changed. Because the diode laser power output can fluctuate, any changes in laser power will show up as increases or decreases in the individual Raman peaks. Examining the intensities of the Raman peaks that change very little with concentration, allows one to use this information to indicate if and when the laser power is changing. The use of these particular peaks does not mean that a routine calibration procedure is not needed; it does mean that the calibration may not have to be performed as often.

Olefin Determination

FIG. 9 illustrates the Raman spectra of two different types of gasoline product. The top curve is the Raman spectrum for a standard unleaded premium gasoline, the lower curve is for a gasoline product called "cat gas." This particular product has a very high olefin content, typically 25 to 30%. It is shown here to illustrate the relative location of the olefin peaks (encircled region) at 1625 $cm^{-1}$ to 1725 $cm^{-1}$. The unleaded gasoline has a fairly low olefin concentration, around 6.5%, so the Raman spectrum for the olefin in the unleaded gasoline is much smaller. It turns out that most of the olefins (C=C double bond) compounds have Raman peaks in the region of 1625 $cm^{-1}$ to 1725 $cm^{-1}$. There may be as many as 50 to 100 different olefin species present in gasoline. It is not necessary to measure each individual olefin component, rather the total olefin concentration as a group is sufficient. The fact that Raman spectra for most of the olefins have at least one peak in this region allows us to measure the area under this curve and determine the total olefin concentration.

Third party chemometric analysis software can be used to develop a calibration model for determining olefin concentration in a manner similar to determining octane rating described above. Once the calibration model is developed and tested, suitable analysis software is developed based on this model.

The multivariate calibration of the model would preferably utilize a maximum likelihood or classical least squares approach to estimate olefin concentrations. A two vector design matrix, confined to wave number regions near the olefin peak(s), would be constructed with a "pure component" olefin vector and a baseline vector. The vectors for the calibration model can be determined by least squares from a series of gasoline standards containing known olefin content, while several functional forms for the baseline are tested for quality of fit. If more than one olefin scattering band is included in the model, then each band can be individually tested for its prediction uncertainty by cross-validation, and the results pooled and weighted by their inverse variances in the final calibration model.

The olefin concentration can be reported by application of the above model in a multivariate least squares step that determines the olefin concentration and baseline amplitude in a sample spectrum. Despite the fact that the olefin analysis requires scattering data only over a few Raman bands, the multichannel nature of the CCD-detected spectrum provides quality assurance on the validity of the model. The magnitude of the residual difference between the best fit model and the measured data would be tested for error in excess of the shot noise in the data; excess error and structure in the residuals (as assessed by an autocorrelation analysis) would indicate the presence of an interfering peak that was not present in the samples used to develop the model; if several olefin bands are used in the analysis, then alternate models could be applied where a poorly-fit band is dropped from the analysis.

FIG. 10 illustrates the Raman spectra of this region (1625 to 1725 $cm^{-1}$) as the olefin concentration is increased from 0.9% to almost 29%. The areas under these curves can be plotted (see FIG. 11) and the data indicate the linear relationship between Raman signal strength and the total olefin concentration. These data can be acquired in seconds, rather than hours as with existing Florescence Indicator Analysis (F.I.A.) technology currently being used in refineries.

Xylene Determination

The three isomers of xylene, meta, ortho, and para, are very valuable as starting materials for petrochemicals. For this reason, they are often removed from gasoline and sold to chemical processing plants. The concentrations of the three individual xylene isomers are difficult to measure quickly and to separate from other contaminating aromatics, such as benzene, toluene, and ethyl benzene. Xylenes are used in such large volume that their rapid and accurate measurement is essential. Current chromatography techniques require nearly fifteen to twenty minutes to analyze for the relative concentrations of the individual isomers. In large chemical processing plants this analysis is just too slow.

Figure 12:
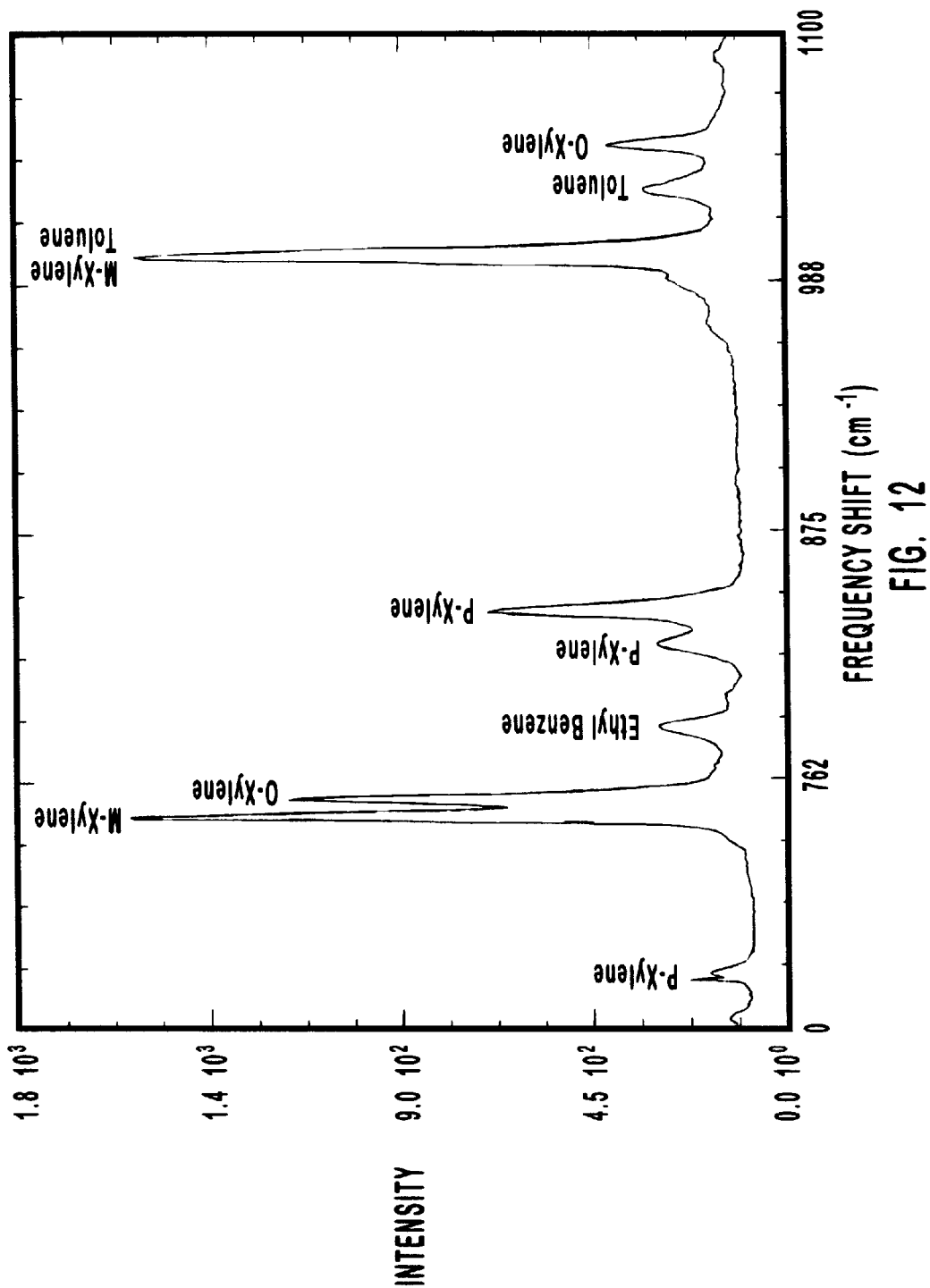
FIG. 12 is a graph of the Raman spectrum of a predistillate fraction rich in xylene illustrating the individual Raman peaks for the various xylene isomers, m-, o-, and p-xylene.

FIG. 12 illustrates the individual Raman peaks for the various xylene isomers, m-, o-, and p-xylene in a predistillate fraction rich in xylene. These components can easily be differentiated from the other commonly occurring aromatics, such as ethyl-benzene, toluene and benzene.

Benzene Concentration Determination

Because benzene is considered a carcinogen, problems surrounding locating its extent, concentration, and safe containment or removal are of utmost concern. EPA Clean Air rules currently in effect require petroleum refiners to reduce benzene levels in gasoline to below 1%. Traditional process chromatography is normally too slow, requiring 15 to 20 minutes per test. Infrared absorption (IR) requires too short of a cell path length, and Near-IR is not sensitive enough. Recent EPA regulations will force a broad range of industries to cut emissions of benzene that pose cancer risks to workers frequently in contact with petroleum products.

Figure 13:
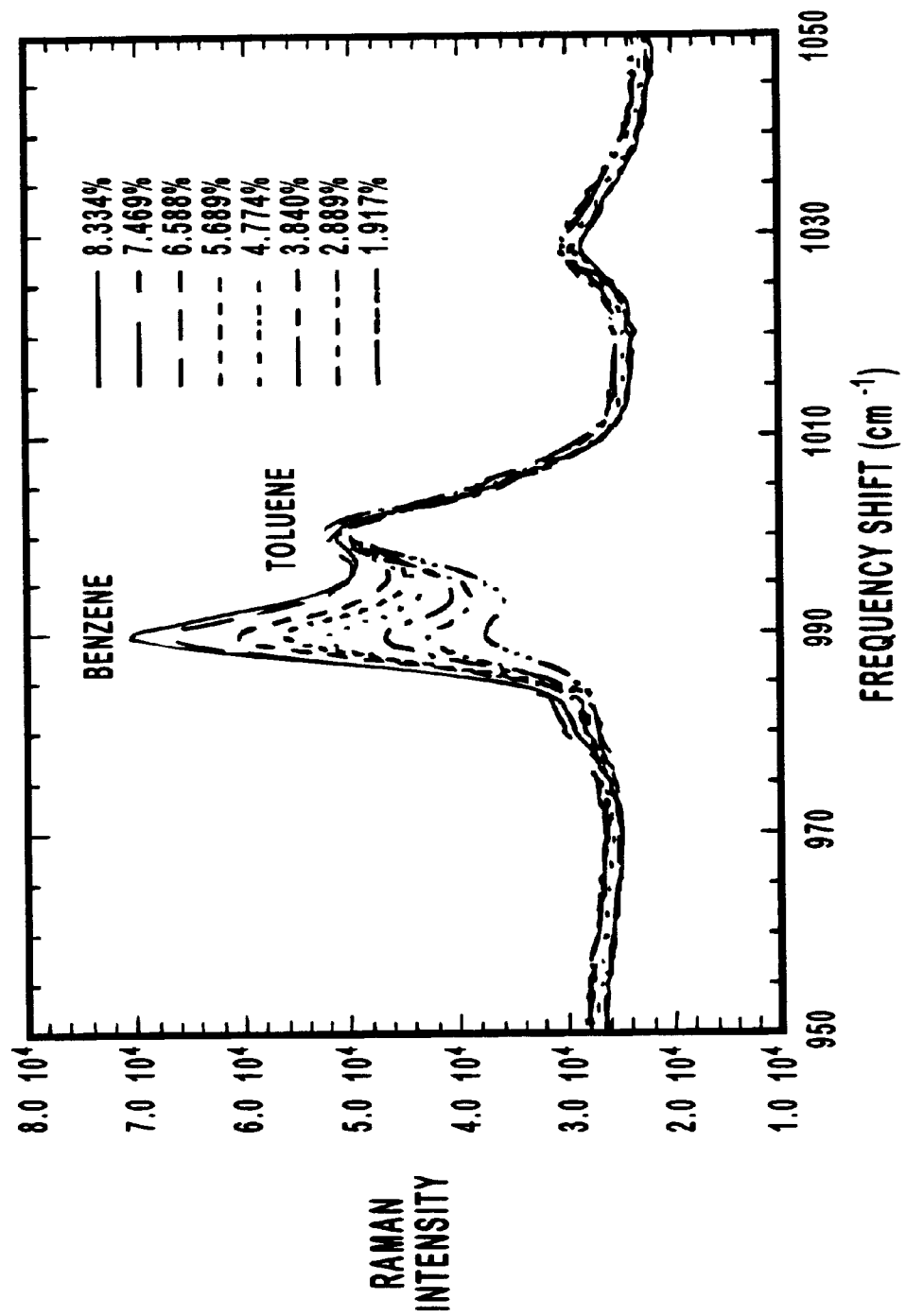
FIG. 13 is a graph of the Raman spectra for increasing concentrations of benzene in unleaded premium gasoline.

FIG. 13 illustrates the Raman spectra for increasing concentrations of benzene in unleaded premium gasoline.

Figure 14:
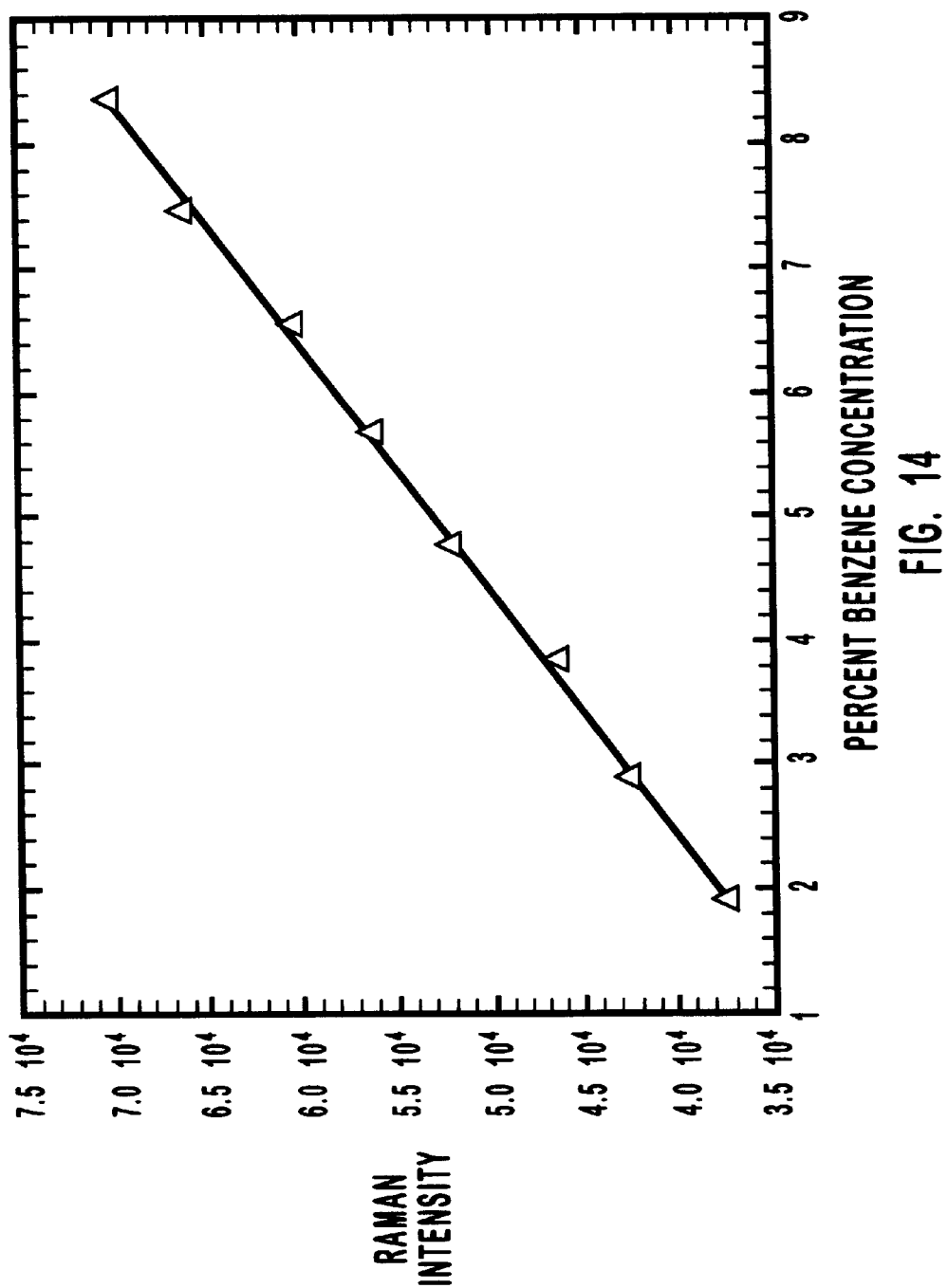
FIG. 14 is a graph of Raman intensity versus the benzene concentration for the curves shown in FIG. 13, indicating a linear relationship between Raman signal strength and the benzene concentration in the gasoline sample.

FIG. 14 illustrates the linear relationship between the area under the Raman benzene peak and the benzene concentration in the gasoline sample.

Fuel Differentiation Application

Figure 15:
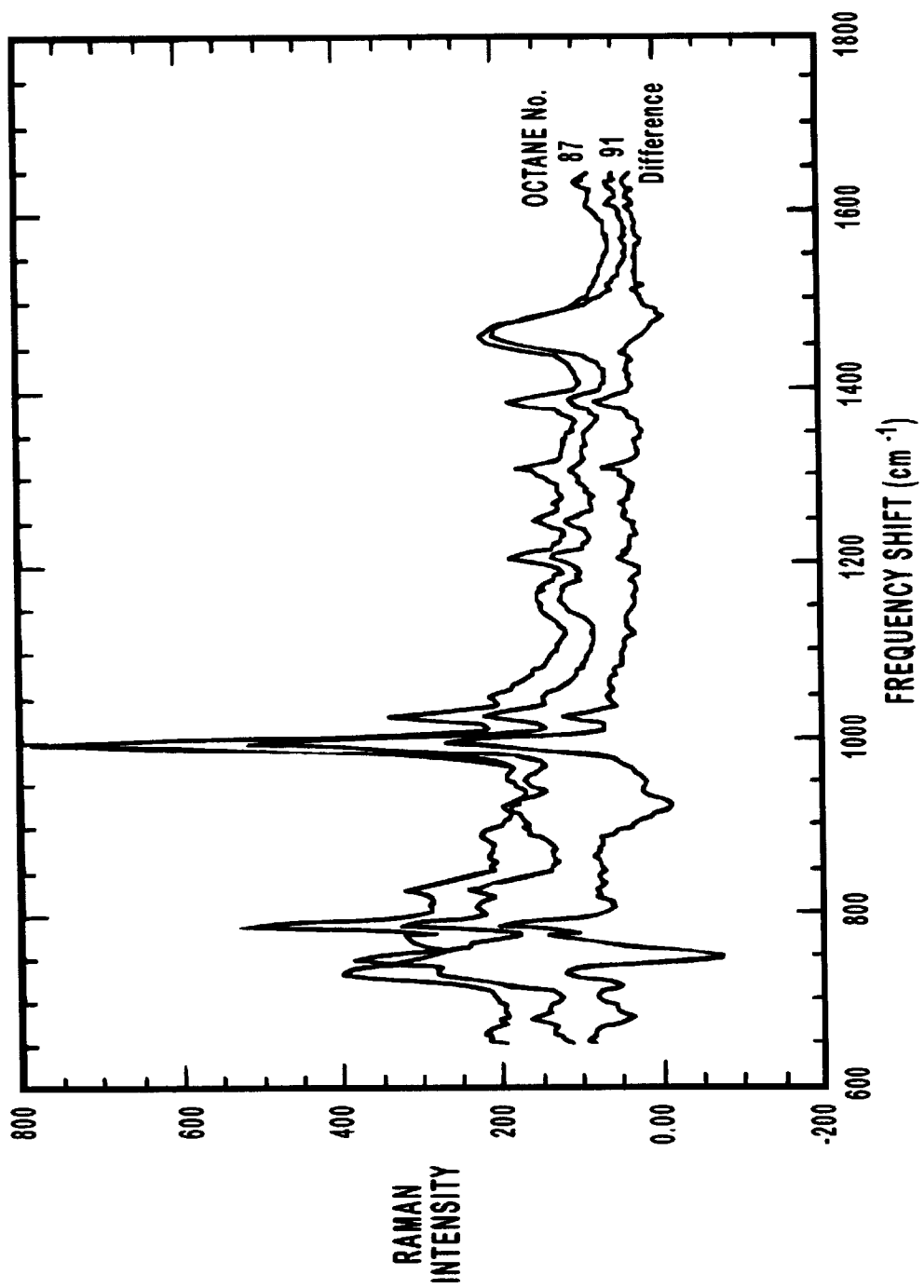
FIG. 15 is a graph of the Raman spectra for two different octane rated gasolines and the subtracted Raman spectrum of the two Raman spectra.

FIG. 15 illustrates the subtraction of two different octane rated gasolines. Since the Raman spectra are different for different fuel formulations, their difference spectra can be used to verify or substantiate that indeed two fuel systems are the same or different from one another. It is not easy for petroleum manufacturers to readily determine if a fuel sample was manufactured by them or their competitor. The ability to compare complete Raman spectra make it relatively easy to test two different fuels and determine how similar they are to one another.

Figure 16:
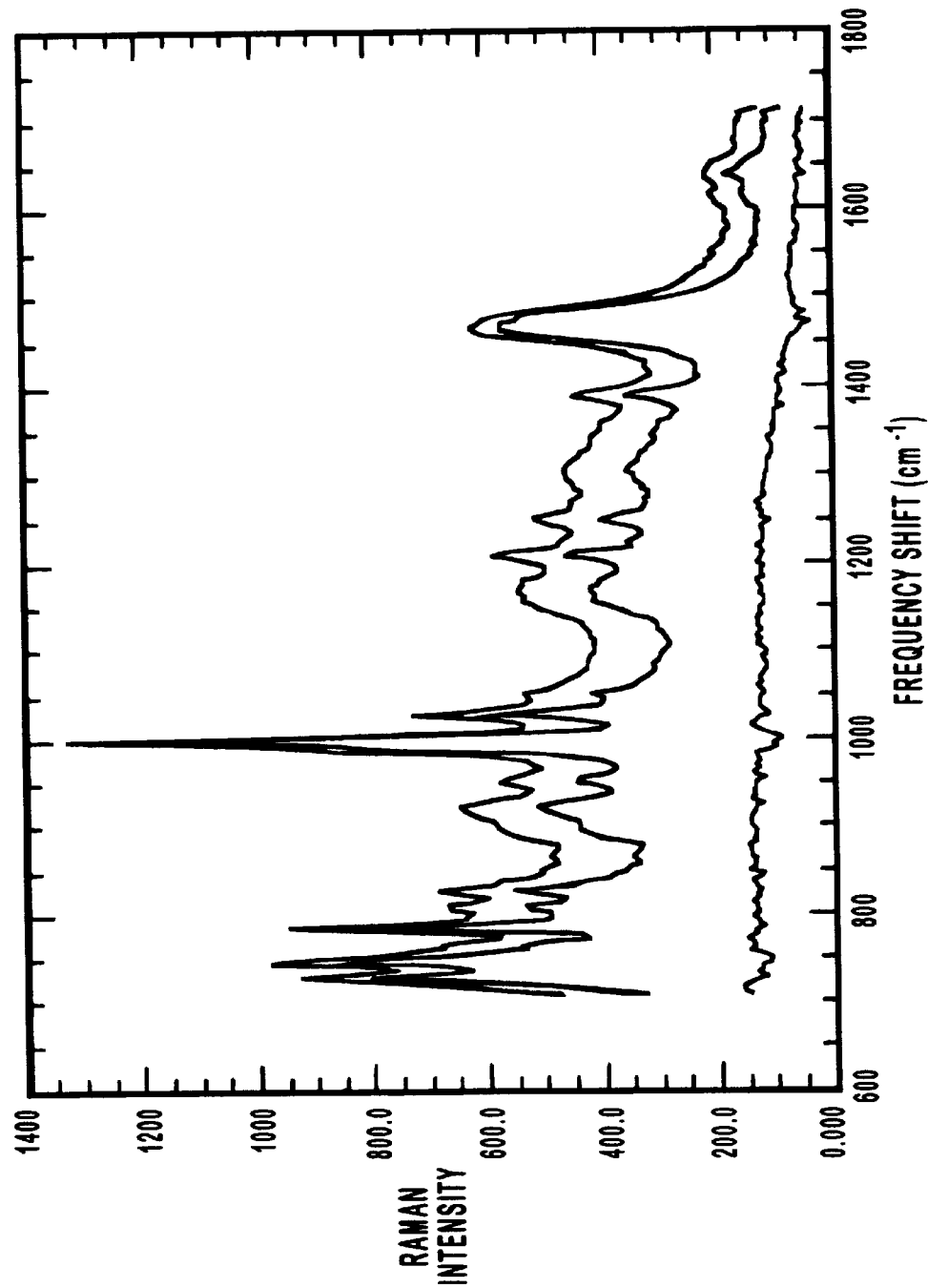
FIG. 16 is a graph of the Raman spectra for two fuel samples from the same manufacturer having the same octane rating and the subtracted Raman spectrum of the two Raman spectra.

FIG. 16 illustrates this same subtraction process applied to two samples of fuel that are in fact the same. The subtracted spectrum is basically a flat line. This type of analysis can be used in pipelines to rapidly determine when one company's fuel has stopped flowing and another company's fuel has begun, or when one fuel type has been replaced by another. In large transmission lines, many different fuel types and brands are carried together, one right after another. Density measurements are often used to determine when one particular fuel is different from another. The density of diesel is sufficiently different from gasoline that this particular test can be used. However, the density does not change sufficiently between two different brands of gasoline to readily determine the cutoff point. The analysis of cutoff point in a pipe line could easily be determined by Raman analysis according to the present invention.

Figure 17:
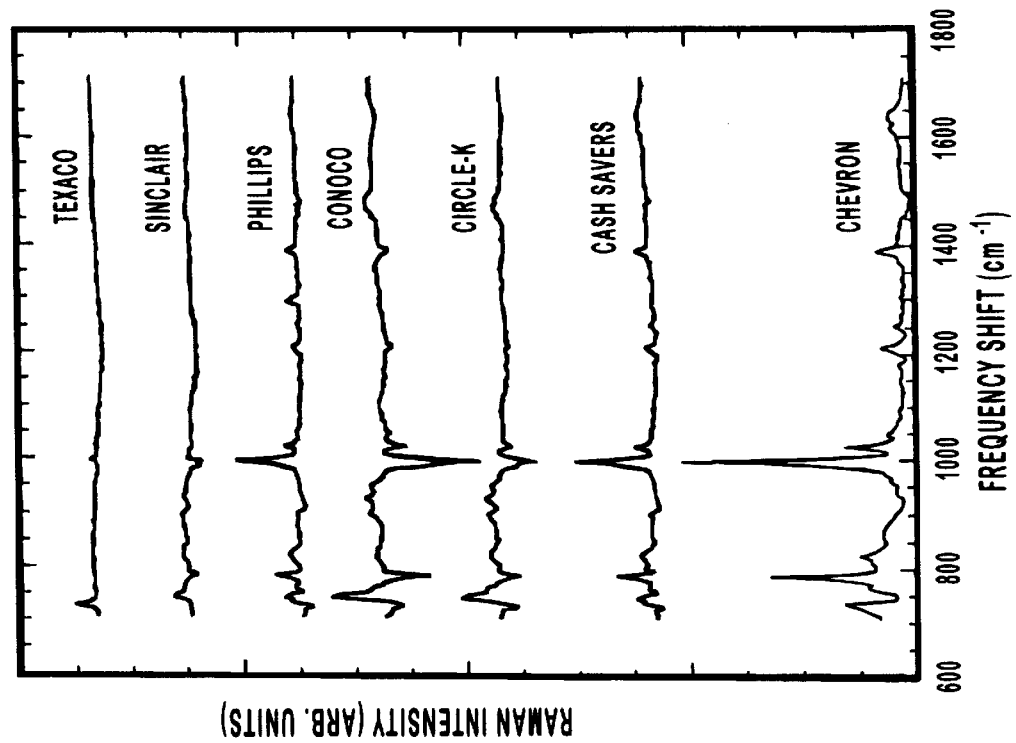
FIG. 17 is a graph of the subtracted Raman spectra for various brands of gasoline subtracted from a single brand of gasoline.

FIG. 17 illustrates the comparison of the subtracted Raman spectra for various brands of gasoline subtracted from a single brand, in this case an Amoco sample. For most of the samples, it was easy to determine that the samples were different, that a Conoco gasoline was different from the Amoco gasoline, etc. Two of the fuels tested have straight lines, indicating that they are identical to the Amoco fuel. It was verified that the Texaco and Sinclair fuel samples tested were made by Amoco. Those two refiners purchased their fuel from a local Amoco refinery rather than transporting their fuel from distant facilities.

Figure 18:
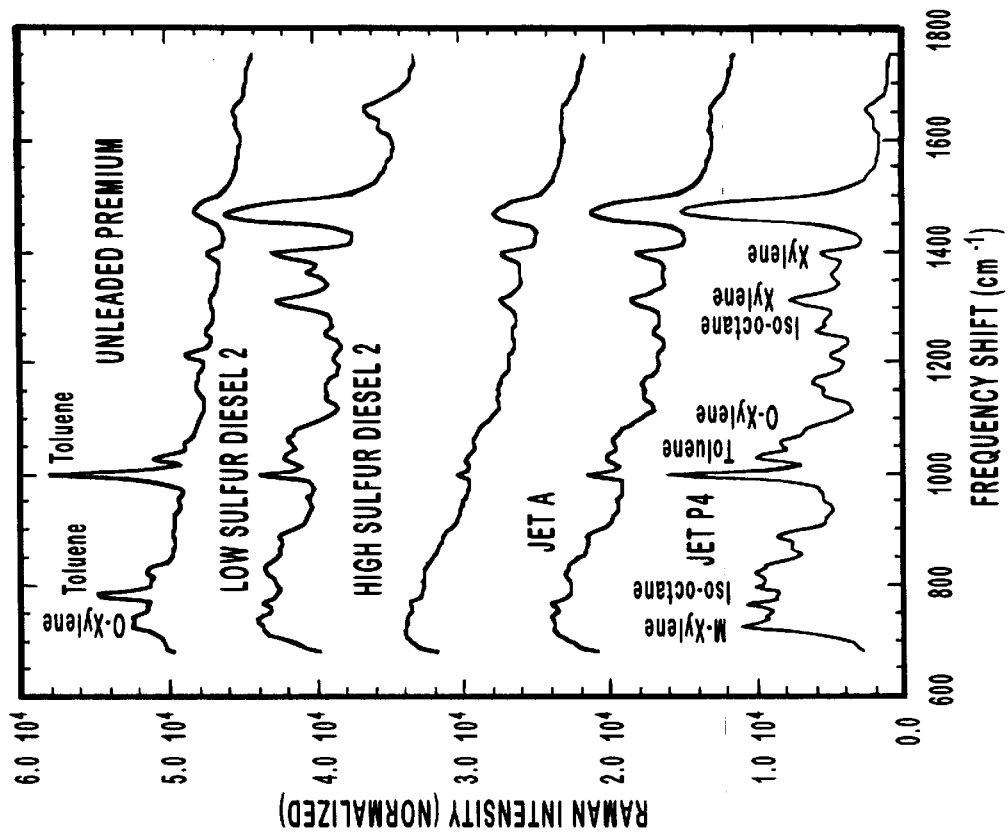
FIG. 18 is a graph of the Raman spectra for different types of fuels indicating the ability to identify the type of fuel from its unique Raman spectrum.

FIG. 18 illustrates the Raman spectra for different types of fuel systems, high and low sulfur diesel, Jet A, Jet JP4, and unleaded premium gasoline. It is apparent that their Raman spectra are unique and can be used to identify the type of fuel.

Alkylation Acid Concentration Determination

FIG. 19 illustrates the Raman spectra for pure sulfuric acid, with a major Raman peak at 920 cm$^{-1}$. FIG. 20 illustrates this same sulfuric acid Raman peak present in a sample of alkylation acid. The Raman spectra for this and other sulfuric acid Raman peaks can be used to determine the actual acid concentration in the alkylation acid process. The acid content is currently determined by conventional titration techniques. The area under the sulfuric acid Raman peaks has a linear relationship to actual acid concentration in the alkylation acid process as illustrated in FIG. 21.

It should be appreciated that the apparatus and method for analyzing the composition of a fluid stream according to the present invention are capable of being incorporated in the form of a variety of embodiments, only a few of which have been illustrated and described above. The invention may be embodied in other forms without departing from its essential characteristics. The described embodiments are to be considered in all respects only as illustrative and not restrictive.

What is claimed is:

1. An external cavity laser comprising:
   one or more diode laser emitters which emit light along a linear optical axis;
   a collimating lens for receiving light from the one or more laser emitters, said collimating lens having a diameter sufficiently large to capture light emitting from the one or more laser emitters; and
   a retro-reflection volume holographic grating positioned along the optical axis to receive light from the collimating lens, said grating being oriented at a non-normal angle relative to the light from the collimating lens, said grating diffracting first order emitted light along the optical axis to provide optical feedback to the one or more laser emitters for frequency stabilization of the light emitted by the one or more laser emitters, wherein zeroth order emitted light passes through said grating along the optical axis as laser output.

2. An external cavity laser as defined in claim 1, wherein the one or more laser emitters produce light having an excitation wavelength in the range from about 200 nm to about 1550 nm.

3. An external cavity laser as defined in claim 1, wherein the one or more laser emitters produce light having an excitation wavelength in the range from about 450 nm to about 1100 nm.

4. An external cavity laser as defined in claim 1, wherein the one or more laser emitters produce light having an excitation wavelength in the range from about 670 nm to about 850 nm.

5. An external cavity laser as defined in claim 1, wherein the one or more laser emitters have a stripe length in the range from about 3 μm to 1 cm.

6. An external cavity laser as defined in claim 1, wherein the one or more laser emitters have a stripe length in the range from about 3 ∞m to 500 μm.

7. An external cavity laser as defined in claim 1, wherein the one or more laser emitters produce a cone-shaped emission pattern in the range from 300 to 450.

8. An external cavity laser as defined in claim 1, wherein the focusing lens directs light into an optical fiber having an acceptance cone, and wherein the focusing lens has a numerical aperture less than said acceptance cone of said optical fiber.

9. An external cavity laser as defined in claim 8, wherein the numerical aperture of the focusing lens is in the range from 0.2 to 0.3.

10. An external cavity laser as defined in claim 1, wherein the collimating lens has a focal length greater than 4 mm, and preferably in the range from 8 mm to 10 mm.

11. An external cavity laser as defined in claim 1, wherein the collimating lens has a numerical aperture in the range from 0.5 to 0.6.

12. An external cavity laser as defined in claim 1, wherein the light from the one or more laser emitters has a linewidth up to 300 GHz.

13. An external cavity laser as defined in claim 1, wherein the light from the one or more laser emitters has a linewidth less than 30 GHz.

14. An external cavity laser as defined in claim 1, wherein the retro-reflection volume holographic grating has between 1200 and 2400 grooves/mm.

15. An external cavity laser as defined in claim 1, wherein the retro-reflection volume holographic grating has between 1700 and 1900 grooves/mm.

16. An external cavity laser as defined in claim 1, wherein the retro-reflection volume holographic grating has at least 600 grooves/mm.

17. An external cavity laser as defined in claim 1, further comprising a focusing lens for receiving light from the retro-reflection volume holographic grating.

18. An external cavity laser as defined in claim 1, wherein the retro-reflection volume holographic grating provides from 15% to 85% feedback to the laser emitters.

19. An external cavity laser comprising:
   one or more diode laser emitters emitting light having an excitation wavelength;
   a collimating lens for receiving light from the one or more laser emitters, said collimating lens having a diameter sufficiently large to capture light emitting from the one or more laser emitters;
   a volume holographic transmission grating positioned to receive light from the collimating lens, said grating being oriented at a non-normal angle relative to the light from the collimating lens, said volume holographic transmission grating having a plurality of grooves oriented parallel to the one or more laser emitters; and
   a power buildup cavity comprising two opposing mirrors, wherein one mirror is positioned to receive first order diffracted light from the volume holographic transmission grating and to reflect light back to the volume holographic diffraction grating to provide optical feedback to the one or more laser emitters.

20. An apparatus as defined in claim 19, wherein the volume holographic diffraction grating provides from 15% to 30% feedback to the one or more laser emitters.

21. An apparatus for analyzing a sample using Raman spectroscopy comprising:
   an external cavity laser source for producing light having an excitation wavelength, wherein the external cavity laser source comprises:
      one or more diode laser emitters which emit light having an excitation wavelength along a linear optical axis;
      a collimating lens for receiving light from the one or more laser emitters, said collimating lens having a diameter sufficiently large to capture light emitting from the one or more laser emitters; and
      a retro-reflection volume holographic diffraction grating positioned along the optical axis to receive light from the collimating lens, said grating being oriented at a non-normal angle relative to the light from the collimating lens, said grating reflecting first order emitted light along the optical axis to provide optical feedback to the one or more laser emitters, wherein a zeroth order emitted light passes through said grating along the optical axis as laser output;
   a Raman sample cell comprising a sample stream inlet and a sample stream outlet for continuous sample flow through the sample cell;
   means for directing light from the laser source into the Raman sample cell;
   an optical connector for connecting one or more collection optical fibers to the sample cell for receiving scattered light from the sample cell;
   a Raman spectrometer comprising:
      an array of the one or more collection optical fibers for transmitting scattered light from the sample cell as an optical signal;
      a filter for rejecting portions of the optical signal having the excitation wavelength;
      a spectrometer grating to disperse the optical signal; and
      a light sensor for converting the optical signal into a corresponding electronic signal; and
      a computer for converting the electronic signal into a representation of the chemical analysis of the sample stream.

22. An apparatus as defined in claim 21, wherein the Raman sample cell further comprises an absorption filter which absorbs light having the excitation wavelength.

23. An apparatus as defined in claim 22, wherein the absorption filter is oriented at angle to minimize reflection of the light directed into the Raman sample cell back to the one or more collection optical fibers.

24. An apparatus as defined in claim 21, wherein the external cavity laser source further comprises a focusing lens for receiving and focusing light from the laser source volume holographic diffraction grating.

25. An apparatus as defined in claim 24, wherein the focusing lens focusses light into an optical fiber and wherein said optical fiber directs light from the laser source into the Raman sample cell.

26. An apparatus as defined in claim 24, wherein the focusing lens focusses light into the Raman sample cell.

27. An apparatus as defined in claim 21, wherein the one or more laser emitters have a stripe length in the range from about 3 $\mu$m to 1 cm.

28. An apparatus as defined in claim 21, wherein the collimating lens has a focal length greater than 4 mm, and preferably in the range from 8 mm to 10 mm.

29. An apparatus as defined in claim 21, wherein the spectrometer grating has between 1200 and 2400 grooves/mm.

30. An apparatus as defined in claim 21, wherein the spectrometer grating has between 1700 and 1900 grooves/mm.

31. An apparatus as defined in claim 21, wherein the light from the one or more laser emitters has a linewidth less than 30 GHz.

32. An apparatus as defined in claim 21, wherein the light from the one or more laser emitters has a linewidth up to 300 GHz.

33. An apparatus as defined in claim 21, wherein the laser source volume holographic diffraction grating has at least 600 grooves/mm.

34. An apparatus as defined in claim 21, wherein the light has an excitation wavelength in the range from about 200 nm to about 1550 nm.

35. An apparatus as defined in claim 21, wherein the light has an excitation wavelength in the range from about 450 nm to about 1100 nm.

36. An apparatus as defined in claim 21, wherein the spectrometer grating is a volume holographic transmission grating.

37. An apparatus for analyzing a sample using Raman spectroscopy comprising:
   an external cavity laser source for producing light having an excitation wavelength, wherein the external cavity diode laser comprises:
      one or more diode laser emitters which emit light along a linear optical axis;
      a collimating lens for receiving light from the one or more laser emitters, said collimating lens having a diameter sufficiently large to capture light emitting from the one or more laser emitters; and
      a volume holographic transmission grating positioned along the optical axis to receive light from the collimating lens, said grating being oriented at a non-normal angle relative to the light from the collimating lens, said volume holographic transmission grating having a plurality of grooves oriented parallel to the one or more laser emitters;

a mirror positioned to receive first order diffracted light from the volume holographic transmission grating and to reflect said first order diffracted light back to the volume holographic transmission grating to provide optical feedback to the one or more laser emitters for frequency stabilization of the one or more laser emitters, wherein zeroth order emitted light passes through said grating along the optical axis as laser output;

a Raman sample cell comprising a sample stream inlet and a sample stream outlet for continuous sample flow through the sample cell;

means for directing light from the laser source into the Raman sample cell;

an optical connector for connecting one or more collection optical fibers to the sample cell for receiving scattered light from the sample cell;

a Raman spectrometer comprising:
  an array of the one or more collection optical fibers for transmitting scattered light from the sample cell as an optical signal;
  a filter for rejecting portions of the optical signal having the excitation wavelength;
  a spectrometer grating to disperse the optical signal; and
  a light sensor for converting the optical signal into a corresponding electronic signal; and
  a computer for converting the electronic signal into a representation of the chemical analysis of the sample stream.

38. An apparatus as defined in claim 37, wherein the Raman sample cell further comprises an absorption filter which absorbs light having the excitation wavelength.

39. An apparatus as defined in claim 38, wherein the absorption filter is oriented at angle to minimize reflection of the light directed into the Raman sample cell back to the one or more collection optical fibers.

40. An apparatus as defined in claim 37, further comprising a focusing lens for receiving and focusing light from the volume holographic transmission grating.

41. An apparatus as defined in claim 40, wherein the focusing lens focusses light into an optical fiber and wherein said optical fiber directs light from the laser source into the Raman sample cell.

42. An apparatus as defined in claim 40, wherein the focusing lens focusses light into the Raman sample cell.

43. An apparatus as defined in claim 37, wherein the volume holographic transmission grating focusses light into an optical fiber and wherein said optical fiber directs light from the larger source into the Raman sample cell.

44. An apparatus as defined in claim 37, wherein the volume holographic transmission grating focusses light into the Raman sample cell.

45. An apparatus as defined in claim 37, wherein the one or more laser emitters produce light having an excitation wavelength in the range from about 200 nm to about 1550 nm.

46. An apparatus as defined in claim 37, wherein the one or more laser emitters produce light having an excitation wavelength in the range from about 450 nm to about 1100 nm.

47. An apparatus as defined in claim 37, wherein the one or more laser emitters have a stripe length in the range from about 3 $\mu$m to 1 cm.

48. An apparatus as defined in claim 37, wherein the one or more laser emitters have a stripe length in the range from about 3 $\mu$m to 500 $\mu$m.

49. An apparatus as defined in claim 37, wherein the light from the one or more laser emitters has a linewidth up to 300 GHz.

50. An apparatus as defined in claim 37, wherein the light from the one or more laser emitters has a linewidth less than 30 GHz.

a computer for converting the electronic signal into a representation of the chemical analysis of the sample stream.

51. An apparatus as defined in claim 37, wherein the spectrometer grating is a volume holographic transmission grating.

52. An external cavity laser comprising:
  one or more diode laser emitters emitting light having an excitation wavelength along a linear optical axis;
  a collimating lens for receiving light from the one or more laser emitters, said collimating lens having a diameter sufficiently large to capture light emitting from the one or more laser emitters;
  a volume holographic transmission grating positioned to receive light from the collimating lens, said grating being oriented at a non-normal angle relative to the light from the collimating lens, said volume holographic transmission grating having a plurality of grooves oriented parallel to the one or more laser emitters; and
  a mirror positioned to receive first order diffracted light from the volume holographic transmission grating and to reflect said first order diffracted light back to the volume holographic transmission grating to provide optical feedback to the one or more laser emitters, wherein zeroth order emitted light passes through said grating along the optical axis as laser output.

53. An external cavity laser as defined in claim 52, wherein the external cavity laser is tuned by rotating the mirror.

* * * * *

(Also Form PTO-1050)

UNITED STATES PATENT AND TRADEMARK OFFICE
CERTIFICATE OF CORRECTION

PATENT NO    :   6,100,975
DATED        :   August 8, 2000
INVENTOR(S)  :   Smith et al.

It is certified that error appears in the above-identified patent and that said Letters Patent are hereby corrected as shown below:

In Column 9, Line 10, please delete "33" and replace it therefor with --X--.

In Column 18, Line 10, please delete "∞" and replace it therefor with --$\mu$--.

In Column 18, Line 38, please delete "300 to 450" and replace it therefor with --30° to 45°--

In Column 21, Line 54 please delete "larger" and replace it therefor with --laser--.

Signed and Sealed this

Twenty-ninth Day of May, 2001

*Attest:*

NICHOLAS P. GODICI

*Attesting Officer*    *Acting Director of the United States Patent and Trademark Office*